(12) United States Patent
Kodandaramaiah et al.

(10) Patent No.: US 9,498,293 B2
(45) Date of Patent: Nov. 22, 2016

(54) AUTOMATED CELL PATCH CLAMPING METHOD AND APPARATUS

(71) Applicants: Suhasa Bangalore Kodandaramaiah, Somerville, MA (US); Edward Stuart Boyden, Chestnut Hill, MA (US); Craig Richard Forest, Atlanta, GA (US)

(72) Inventors: Suhasa Bangalore Kodandaramaiah, Somerville, MA (US); Edward Stuart Boyden, Chestnut Hill, MA (US); Craig Richard Forest, Atlanta, GA (US)

(73) Assignees: Massachusetts Institute of Technology, Cambridge, MA (US); Georgia Tech Research Corporation, Atlanta, GA (US)

( * ) Notice: Subject to any disclaimer, the term of this patent is extended or adjusted under 35 U.S.C. 154(b) by 145 days.

(21) Appl. No.: 14/079,630

(22) Filed: Nov. 13, 2013

(65) Prior Publication Data
US 2014/0228857 A1 Aug. 14, 2014

Related U.S. Application Data

(63) Continuation-in-part of application No. 13/676,082, filed on Nov. 13, 2012.

(60) Provisional application No. 61/558,841, filed on Nov. 11, 2011, provisional application No. 61/726,008, filed on Nov. 13, 2012.

(51) Int. Cl.
| | |
|---|---|
| *A61B 5/053* | (2006.01) |
| *A61B 19/00* | (2006.01) |
| *A61B 5/00* | (2006.01) |
| *A61B 5/04* | (2006.01) |

(52) U.S. Cl.
CPC ....... *A61B 19/2203* (2013.01); *A61B 5/04001* (2013.01); *A61B 5/0538* (2013.01); *A61B 5/6885* (2013.01); *A61B 34/32* (2016.02); *A61B 2503/40* (2013.01)

(58) Field of Classification Search
CPC A61B 18/14; A61B 5/6885; A61B 5/05001; A61B 19/2003; A61B 5/0538; A61B 2503/40
See application file for complete search history.

(56) References Cited

U.S. PATENT DOCUMENTS

2012/0027807 A1* 2/2012 Chien ................. A61L 27/3804
424/400
2012/0083861 A1* 4/2012 Fried .................. A61N 1/36171
607/76

OTHER PUBLICATIONS

Mandi Azizian, Student Member, IEEE, Rajni Patel, Fellow, IEEE, Cezar Gavrilovici and Michael Poulter, Computer-Assisted Patch Clamping, 2010 IEEE International Conference on Robotics and Automation, Anchorage Convention District, May 3-8, 2010, Anchorage, Alaska, USA, pp. 4131-4136.*

*Primary Examiner* — Sean Dougherty
(74) *Attorney, Agent, or Firm* — Norma E. Henderson

(57) ABSTRACT

In an automated method for in vivo multiple cell patch clamping, cell patch clamping devices are automatically moved into position and targeted to multiple corresponding cells. Cell contact is determined by analyzing the temporal series of measured resistance levels at the clamping devices as they are moved. The difference between successive resistance levels is computed and compared to a threshold, which must be exceeded for a minimum number of computations before neuron contact is assumed. Pneumatic control methods are used to achieve cell-attached or gigaseal formation and subsequent cell break-in, leading to whole-cell patch clamp formation. An automated robotic system automatically performs patch clamping in vivo, automatically detecting cells according to the methodology by analyzing the temporal sequence of electrode impedance changes. By continuously monitoring the patching process and rapidly executing actions triggered by specific measurements, the robot can rapidly find neurons in the living brain and establish recordings.

20 Claims, 17 Drawing Sheets

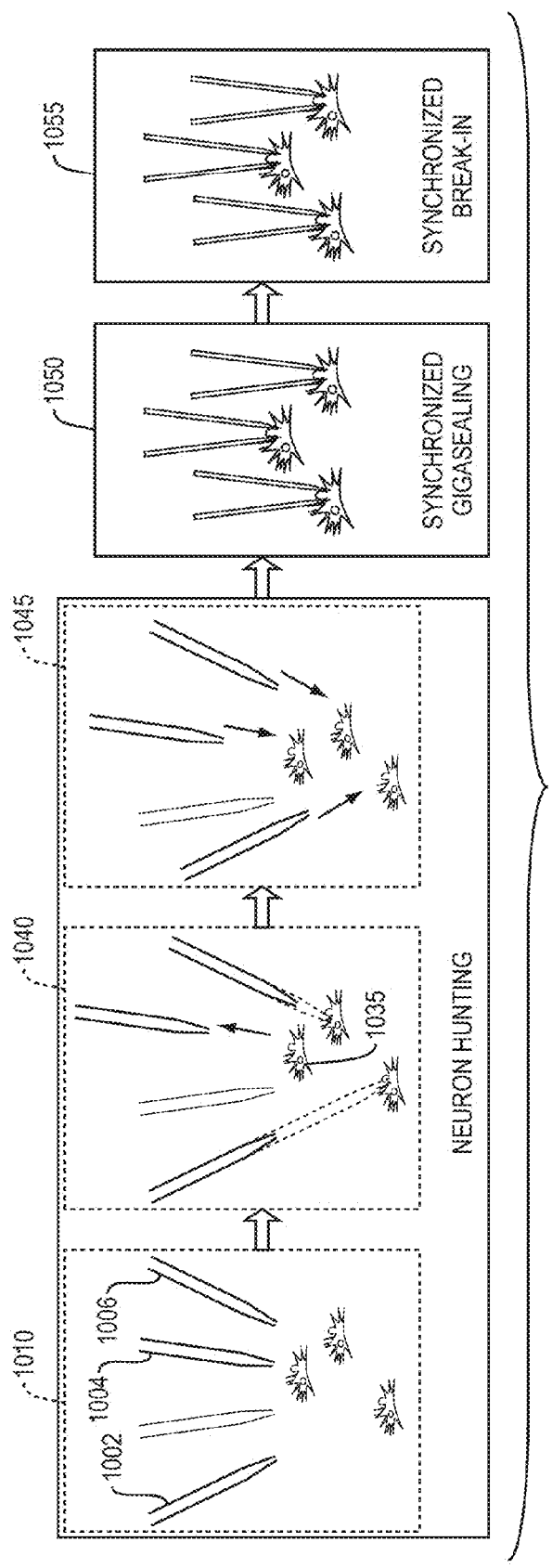

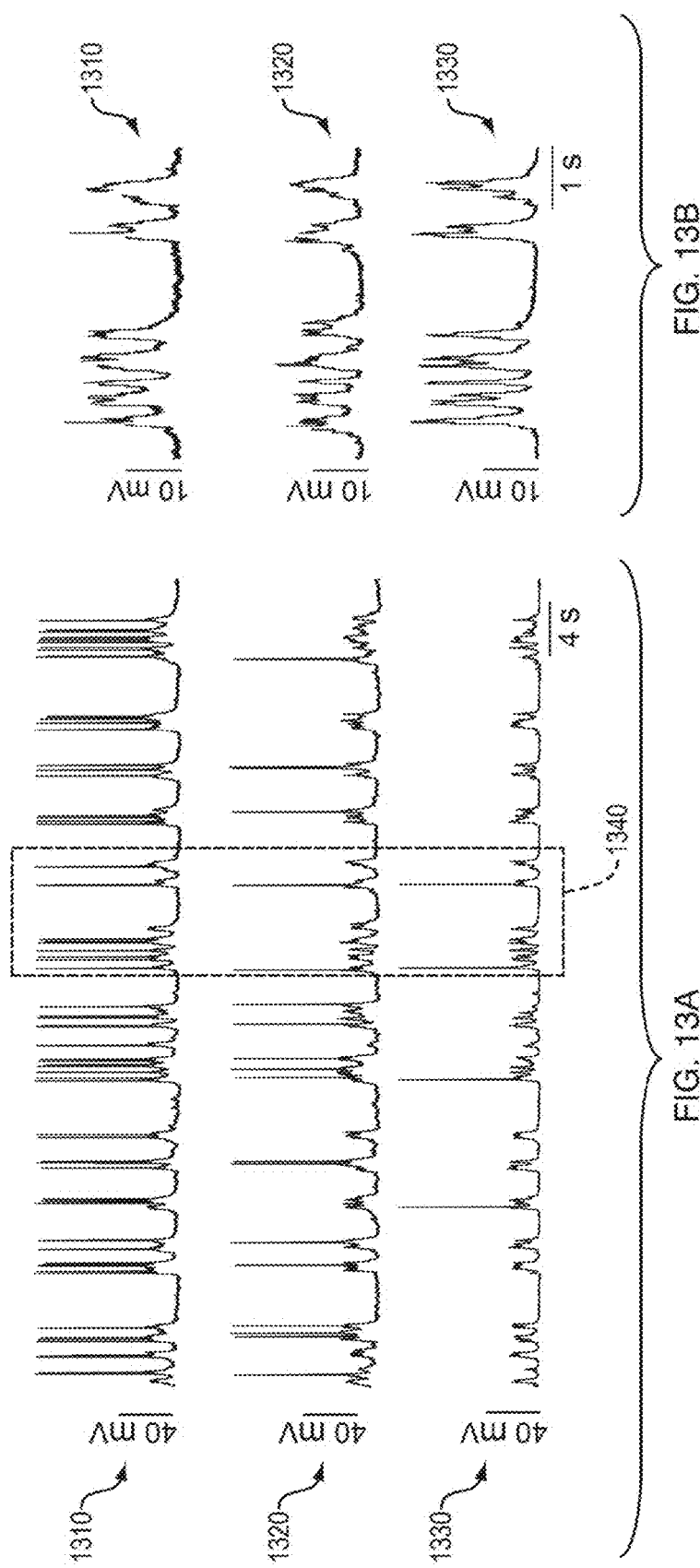

AUTOMATED CELL PATCH CLAMPING METHOD AND APPARATUS

RELATED APPLICATIONS

This application claims the benefit of U.S. Provisional Application Ser. No. 61/726,008, filed Nov. 13, 2012, the entire disclosure of which is herein incorporated by reference.

This application is also a continuation-in-part of U.S. patent application Ser. No. 13/676,082, filed Nov. 13, 2012, which claims the benefit of U.S. Provisional Application Ser. No. 61/558,841, filed Nov. 11, 2011, the entire disclosures of which are herein incorporated by reference.

STATEMENT REGARDING FEDERALLY SPONSORED RESEARCH OR DEVELOPMENT

This invention was made with U.S. government support under Grant Numbers OD002002, NS075421, 1 EY023173, and NS067199, awarded by National Institutes of Health, and Grant Number EFRI 0835878, awarded by the National Science Foundation. The government has certain rights in this invention.

FIELD OF THE TECHNOLOGY

The present invention relates to whole-cell patch clamp electrophysiology and, in particular, to an automated in vivo whole-cell patch clamp apparatus and method.

BACKGROUND

Whole-cell patch clamp electrophysiology of neurons is a "gold standard" technique for high-fidelity analysis of the biophysical mechanisms of neural computation and pathology. Whole-cell patch clamp electrophysiology of neurons in vivo enables the recording of electrical events in cells with great precision and supports a wide diversity of morphological and molecular analysis experiments important for the understanding of single-cell and network functions in the intact brain. However, high levels of skill are required in order to perform in vivo patching, and the process is time-consuming and painstaking.

In whole-cell patch clamp electrophysiology, a glass pipette electrode is used to gain electrical and molecular access to the inside of a cell. It permits high-fidelity recording of electrical activity in neurons embedded within intact tissue, such as in brain slices, or in vivo. Whole-cell patch clamp recordings [Hamill, O. P., Marty, A., Neher, E., Sakmann, B. & Sigworth, F. J. Improved patch-clamp techniques for high-resolution current recording from cells and cell-free membrane patches. *Pflugers Arch* 391, 85-100 (1981); Margrie, T. W., Brecht, M. & Sakmann, B. In vivo, low-resistance, whole-cell recordings from neurons in the anaesthetized and awake mammalian brain. *Pflugers Arch* 444, 491-498 (2002)] of the electrical activity of neurons in vivo, which utilize the glass micropipettes to establish electrical and molecular access to the insides of neurons embedded in intact tissue, exhibit signal quality and temporal fidelity sufficient to report synaptic and ion-channel mediated subthreshold events of importance for understanding how neurons compute, and how their physiology can be modulated by brain disorders or pharmaceuticals. In vivo patching of cells in intact brain presents several capabilities that make it of great use: the recordings present extremely high signal-to-noise ratios and thus can be used to reveal subthreshold responses such as synaptic or ion channel events. Current can be delivered into a pipette to drive or silence the cell being recorded, or to support the characterization of specific receptors or channels in the cell.

Whole-cell patch clamping of cells in intact tissue also allows for infusion of chemicals and the extraction of cell contents. Molecular access to the cell enables infusion of dyes for morphological visualization, as well as extraction of cell contents for transcriptomic single-cell analysis [Eberwine, J. et al. Analysis of gene expression in single live neurons. *Proc Natl Acad Sci USA* 89, 3010-3014 (1992)], thus enabling integrative analysis of molecular, anatomical, and electrophysiological information about single neurons in intact tissue.

However, whole-cell patch clamping of cells in intact tissue is laborious, being something of an art to perform, especially in vivo. Although protocols exist for performing whole-cell patch clamp recording in such conditions, much practice is required by individual investigators to master the technique, since each step in the process of looking for a neuron and establishing the recording requires intuition as well as fast judgment and action. This has limited adoption in neuroscience to a small number of labs, and also precludes systematic and scalable in vivo patch clamping experiments.

SUMMARY

A robot and method for parallel patch clamping of multiple neurons in vivo, known as the "Multipatcher", is described. In one aspect, a simple robot automatically performs parallel cell patch clamping in vivo, automatically detecting cells by analyzing the temporal sequence of electrode impedance changes. It demonstrates good yield, throughput, and quality of recording in mouse cortex and hippocampus. In another aspect, the present invention is a straightforward automated methodology for carrying out in vivo patch clamping, and an automated robotic system capable of performing this methodology. By continuously monitoring the patching process and rapidly executing actions triggered by specific measurements, the robot can rapidly find neurons in the living brain and establish recordings. The performance of the robot has been validated in both the cortex and hippocampus of anesthetized mice. The robot achieves yields, cell recording qualities, and operational speeds that are comparable to, or exceed, those of experienced human investigators. This "multipatcher" robot not only makes broadly accessible a high-performance scalable physiological technique, but also enables systematic assessments of single cells within neural circuits. It also provides a powerful scalable platform for performing single-cell analyses in other kinds of intact tissue, both natural and engineered.

In one aspect, the present invention is therefore a method for automated whole-cell patch clamping using an automated apparatus for cell patch clamping. The method includes the steps of localizing the electrodes of a group of associated cell patch clamping devices by causing the tips of the electrodes to be moved to an appropriate location for cell hunting, iteratively moving the tips of the electrodes by a defined amount, measuring an electrical property, such as resistance, at the electrode tips during or after each iteration of the step of moving, determining whether or not at least one target cell has been encountered by constructing a temporal series of the resistance measurements during or after at least one iteration of the steps of moving and measuring, iteratively continuing the steps of moving, measuring, and determining until the temporal series of electrical property measurements for one or more of the electrodes, over a threshold number of consecutive iterations, indicates a predefined signature of electrode change that has passed a pre-set cell detection threshold, pausing the motion of the electrodes, initiating connection formation, assessing whether or not connection formation has been achieved, optionally initiating break-in and formation of whole-cell patch clamps if connection formation has been achieved, and verifying formation of the whole-cell patch clamps.

The method may also include the step of providing strong positive pressure to the cell patch clamping devices during the step of localizing. The method of may also include, after completing the step of localizing, the steps of reducing the pressure provided to the cell patch clamping devices to low positive pressure, measuring the electrical property at the electrode tips, assessing whether or not the measured electrical property has passed a pre-set tip blockage threshold for any electrode, and retracting the associated cell patch clamping device to indicate tip blockage and failure if the measured electrical property has passed the pre-set tip blockage threshold. The step of initiating connection formation may also include the step of releasing the positive pressure applied to the cell patch clamping devices. The method may also include, after the step of assessing, the steps of applying suction pressure to the cell patch clamping devices if connection formation has not been achieved and then re-assessing whether or not connection formation has been achieved. The step of initiating break-in and formation further may further include applying at least one of suction and an electrical pulse to the cell patch clamping devices. The method may also include the step of retracting the cell patch clamping device to indicate cell location failure if a predetermined maximum level for moving the electrode tips has been reached.

In another aspect, the invention is a method for achieving and verifying cell contact in an automated electrophysiology device by localizing the electrodes of the electrophysiology apparatus by causing the tips of the electrodes to be moved to an appropriate location for cell hunting, iteratively moving the tips of the electrodes by a small amount, measuring an electrical property at the electrode tips during or after each iteration of the step of moving, determining whether or not a target cell has been encountered by constructing a temporal series of the electrical property measurements after each iteration of the steps of moving and measuring, and iteratively continuing the steps of moving, measuring, and determining until the temporal series of electrical property measurements for one or more of the electrodes, over a threshold number of consecutive iterations, indicates a predefined signature of electrode change that has passed a pre-set cell detection threshold.

In another aspect, the present invention is an apparatus for automated cell patch clamping. The apparatus includes cell patch formation apparatus, comprising a group of cell patch clamping devices, each device having an associated electrode, a 3-axis linear actuator configured for positioning the cell patch clamping device, a patch amplifier with computer interface, and a programmable linear motor configured for moving the cell patch clamping device in a temporally precise fashion, and a computer interface configured for automated closed-loop control of the programmable motors based upon a temporal series of electrical property measurements made at the tips of the electrodes. The apparatus may also include an automated control system configured for causing the tips of the electrodes to be moved to an appropriate location for cell hunting, iteratively causing the tips of the electrodes to be moved by a defined amount, measuring the electrical property at the electrode tips during or after each iteration of the step of moving, determining whether or not at least one target cell has been encountered by constructing a temporal series of the electrical property measurements after each iteration of the steps of moving and measuring, iteratively continuing the steps of moving, measuring, and determining until the temporal series of electrical property measurements for one or more of the electrodes, over a threshold number of consecutive iterations, indicates a predefined signature of electrode change that has passed a pre-set cell detection threshold, stopping the motion of the electrodes, initiating connection formation, assessing whether or not connection formation has been achieved, optionally initiating break-in and formation of whole-cell patch clamps if connection formation has been achieved, and optionally verifying formation of the whole-cell patch clamps. The apparatus may further include a controllable plurality of pneumatic valves configured for application of pressure and suction to the cell patch clamping devices.

In yet another aspect, the invention is a method for controlling a group of automated cell patch clamping devices. In a cell patch formation apparatus that includes a group of cell patch clamping devices, each device having an associated electrode, a 3-axis linear actuator configured for positioning the cell patch clamping device, a patch amplifier with computer interface, and a programmable linear motor configured for moving the cell patch clamping device in a temporally precise fashion, and a computer interface configured for closed-loop control of the programmable motors based upon sequences of electrical property measurements made at the tips of the electrodes, the method includes localizing the electrodes by causing the linear motors to move the tips of the electrodes to an appropriate location for cell hunting, causing the linear motors to iteratively move the tips of the recording electrodes by a defined amount, measuring an electrical property at the electrode tips during or after each iteration of the step of moving, determining whether or not at least one target cell has been encountered by constructing a temporal series of the electrical property measurements during or after at least one iteration of the steps of moving and measuring, iteratively continuing the steps of moving, measuring, and determining until the temporal series of electrical property measurements for one or more of the electrodes, over a threshold number of consecutive iterations, indicates a predefined signature of electrode change that has passed a pre-set cell detection threshold, causing the linear motors to pause the motion of the electrodes, initiating connection formation, assessing whether or not connection formation has been achieved, if connection formation has been achieved, optionally initiating break-in and formation of at least one whole-cell patch clamp, and optionally verifying formation of the whole-cell patch clamps.

The cell patch formation apparatus may further include a controllable plurality of pneumatic valves configured for application of pressure and suction to the cell patch clamping devices and the method may further include providing strong positive pressure from the controllable plurality of pneumatic valves to the cell patch clamping devices during the step of localizing, reducing the pressure provided to the cell patch clamping devices to low positive pressure after completing the step of localizing, measuring the electrical property at the electrode tips, assessing whether or not the measured electrical property passed a pre-set tip blockage threshold, retracting the associated cell patch clamping devices to indicate tip blockage and failure if the measured electrical property has passed the pre-set tip blockage threshold, releasing the positive pressure applied to the cell patch clamping devices during the step of initiating connection formation, applying suction pressure from the controllable plurality of pneumatic valves to the cell patch clamping devices if connection formation has not been achieved, re-assessing whether or not connection formation has been achieved, and initiating break-in and cell patch clamp formation by applying suction pressure from the controllable plurality of pneumatic valves and/or an electrical pulse to the cell patch clamping devices.

BRIEF DESCRIPTION OF THE DRAWINGS

Other aspects, advantages and novel features of the invention will become more apparent from the following detailed description of the invention when considered in conjunction with the accompanying drawings wherein:

FIGS. 10A-C are visual depictions of the stages of three embodiments of the in vivo multipatching process carried out using the apparatus and methodology of the present invention;

FIGS. 13A and 13B depict exemplary whole cell current clamp recordings and sub-threshold membrane potential fluctuations, respectively, in three neurons that were recorded simultaneously during the trial depicted in FIG. 12.

DETAILED DESCRIPTION

The parent application, U.S. patent application Ser. No. 13/676,082, filed Nov. 13, 2012, is incorporated in its entirety herein. In U.S. patent application Ser. No. 13/676, 082, a method was described by which patch clamping in vivo was reduced to a computer process that controlled the "autopatcher", a robot capable of conducting blind in vivo patch clamping in an automated fashion. The utility of the autopatcher was demonstrated for obtaining recordings in both the cortex and hippocampus of the anesthetized mouse brain, achieving high yields (~30% of overall attempts) and recording qualities that were comparable to those of trained humans. The algorithmic nature of the procedure and the simple robotics needed to implement the autopatcher opened up the ability to actuate many pipettes within a single brain, and to perform parallel recordings of neurons or other cells within a single living network.

Building off the discovery that blind in vivo whole-cell patching could be reduced to a reliable and stereotyped process, the core hardware and software components of the single channel autopatcher were used to develop the "multipatcher", a robot capable patch clamping sets of neurons simultaneously in vivo. An exemplary prototype multipatcher consisting of four independently controlled patch pipettes was constructed. This multipatching robot was capable of achieving stable whole cell recordings from pairs and triplet of neurons, with a 59% success rate of whole cell recordings from one or more neurons, and a 30.7% success rate of recording from two or more neurons. The trials typically took just 2-3 minutes for each channel, and taking 10-11 minutes for a full trial. Simultaneous whole cell recordings could be carried from these neurons for up to 90 minutes. The processss used for multipatching can be generalized to control arbitrarily large number of electrodes; additionally, the high yield, throughput and automation of complex set of tasks enables a practical solution for conducting patch clamp studies in potentially dozens of interconnected neurons in vivo for the first time. This will enable a more systematic assessment of how neurons work together to implement computations, and how they malfunction in diseased states.

The preferred embodiment of the multipatcher robot shares many of its core components with the single channel autopatcher described in U.S. patent application Ser. No. 13/676,082. A schematic depiction of a preferred embodiment of an apparatus according to, and for carrying out, the present invention is shown in FIG. 1, which is a schematic of the robotic system ("the multipatcher") used to perform the multipatching process described later.

Figure 1:
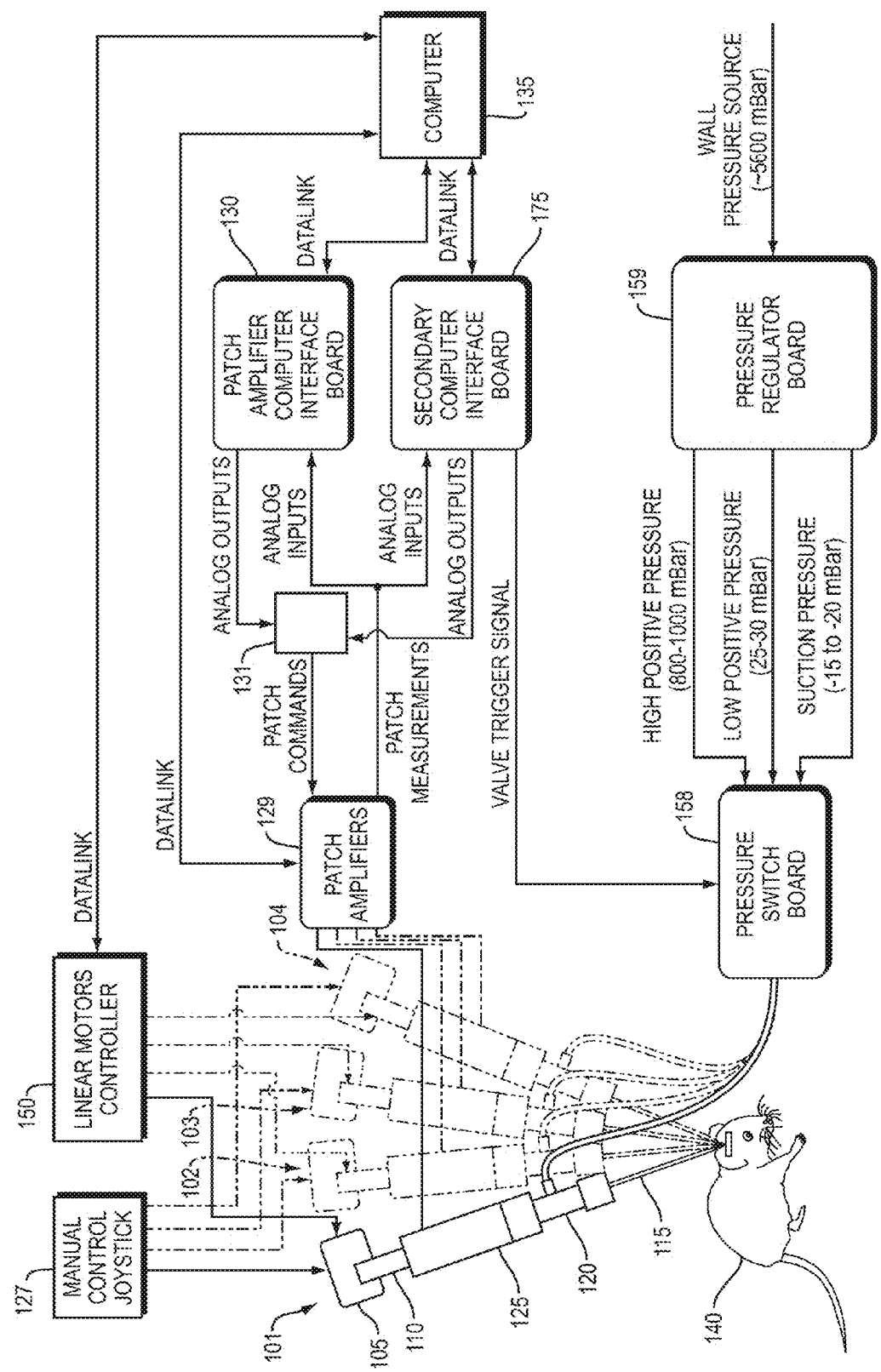
FIG. 1 is a schematic depiction of a preferred embodiment of an apparatus according to, and for carrying out, the present invention.

As shown in FIG. 1, an exemplary embodiment of the system has four end actuator modules 101, 102, 103, 104, each comprising a 3-axis linear actuator 105 and an additional programmable linear motor 110. The system employs a conventional in vivo patch setup, including pipette 115, pipette holder 120, headstage 125 mounted on each end actuator module 101, 102, 103, 104, 3-axis linear actuator 105 with control joystick 127, patch amplifier 129 connected to patch amplifier computer interface board 130 by switch box 131, and computer 135. The apparatus shown in FIG. 1 is set up for patching on headfixed mouse 140. For simplicity, connections from only one such system to the patch amplifier 129, the motors controller 150, and the joystick 127 are highlighted in FIG. 1. The robot of FIG. 1 is equipped with three simple modules: programmable linear motors 110 with linear motors controller 150, which functions to move pipettes 115 up and down in a temporally precise fashion, pressure switch board 158 and pressure regulator board 159 for pressure control, and secondary computer interface board 175 that enables closed-loop control of motors 110 based upon sequences of pipette resistance measurements. If the vertical axis of 3-axis linear actuator 105 is computer-controlled, programmable linear motor 110 with linear motor controller 150 can be omitted, and if patch amplifier 129 plus patch amplifier computer interface board 130 provides direct access to measurements, secondary computer interface board 175 can be omitted.

Each headstage 125 is connected to a patch amplifier 129, which routes the signals to computer 135 via the two computer interface boards, patch amplifier computer interface board 130 and secondary computer interface board 175. Secondary computer interface board 175 is dedicated to data acquisition, while patch amplifier computer interface board 130 is used for executing the multipatching process. The headstages communicate electrically with amplifiers and the computer interface board, which both records the neural signals and delivers neural control signals to the headstages. Actuation of motors is achieved using linear motor controller 150, which is commanded by computer 135, thus completing the closed loop control system. There is a pneumatic pressure control system, consisting of pressure regulation board 159 and pressure switch board 158, which takes in pressurized air stored in a large reservoir and converts that into different regulated pressure states such as high positive pressure, low positive pressure and suction. These regulated pressure states can be applied to the pipettes at different time points during the multipatching process. Pressure switch-board 158, which has a controllable bank of pneumatic valves and analog pressure regulators, is controlled using secondary computer interface board 175.

While specific parts and implementation details are described herein with respect to the embodiment of FIG. 1, it will be clear to one of skill in the art of the invention that many other comparable parts, software, and implementation methodologies exist and would be equally suitable for use in the present invention. It will further be clear to one of skill in the art that the system can easily be scaled up n-fold.

In the prototype embodiment, each recording probe is a glass pipette with a fine tip, filled with conductive saline solution. A silver chloride wire is inserted inside the pipette electrically connects the conductive solution to an amplifying headstage. Each headstage is mounted on a programmable linear motor, which is in turn held in place using a 3-axes linear manipulator. The assembly of the programmable linear motor, and the 3-axes linear manipulator make up the end actuator modules, four of which are arranged in a radial pattern so as to be able to position an array of 4 pipettes, with their distal ends in close proximity to each other.

The robot of FIG. 1 monitors pipette resistance as the pipettes are lowered into the brain, and automatically moves the pipettes in incremental steps via the linear actuator. In one embodiment, the pipette resistance monitoring can be performed by a traditional patch amplifier and digitizer, and the 3-axis linear actuator typically used for in vivo patching can be used as the robotic actuator. For flexibility, an optional additional computer interface board was added to support pipette resistance monitoring, and an additional linear actuator for pipette movement. In some embodiments, the robot employs a set of valves connected to pressure reservoirs to provide positive pressure during pipette insertion into the brain and negative pressure as necessary to result in gigaseal formation and attainment of the whole cell state.

Figure 2:
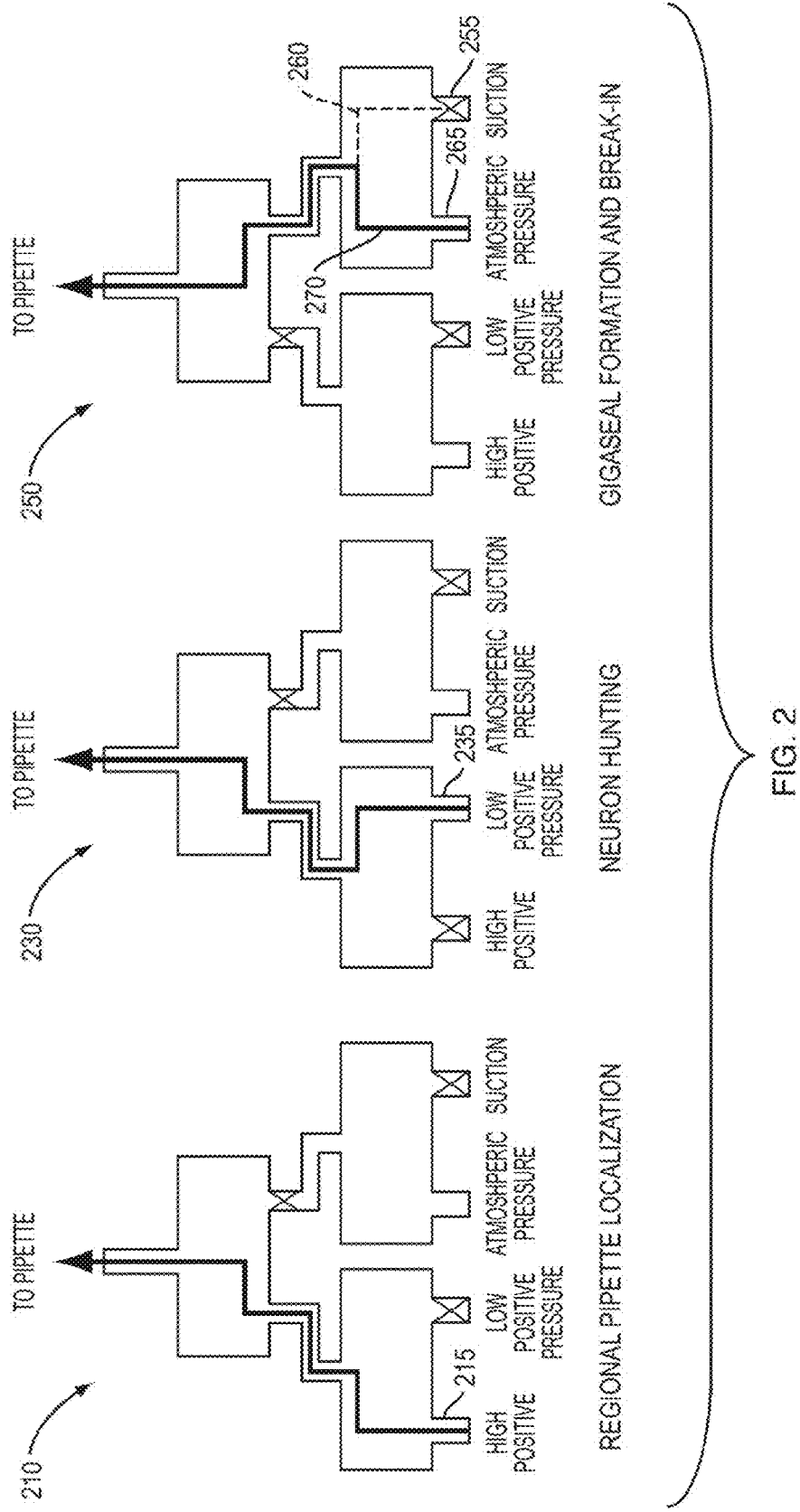
FIG. 2 is a schematic depicting exemplary configurations of pneumatic valve banks employed in the apparatus of FIG. 1 during the stages of multipatcher operation, according to one aspect of the present invention.

FIG. 2 is a schematic depicting the configurations of the pneumatic valve banks during the stages of multipatcher operation. In FIG. 2, "x" represents closed valves and lines depict connectivity of volumes at the same pressure. During regional pipette localization stage 210, positive pressure 215 (800-1,000 mBar) is connected to the pipette. This is also the configuration realized when the valves are not powered. During neuron hunting stage 230, low positive pressure 235 (25-30 mBar) is connected to the pipette. During gigaseal formation stage 250, suction pressure 255 (−15 to −20 mBar; dotted line 260) or atmospheric pressure 265 (solid line 270) is applied. During the break-in stage, suction pressure 255 is also applied.

Figure 3:
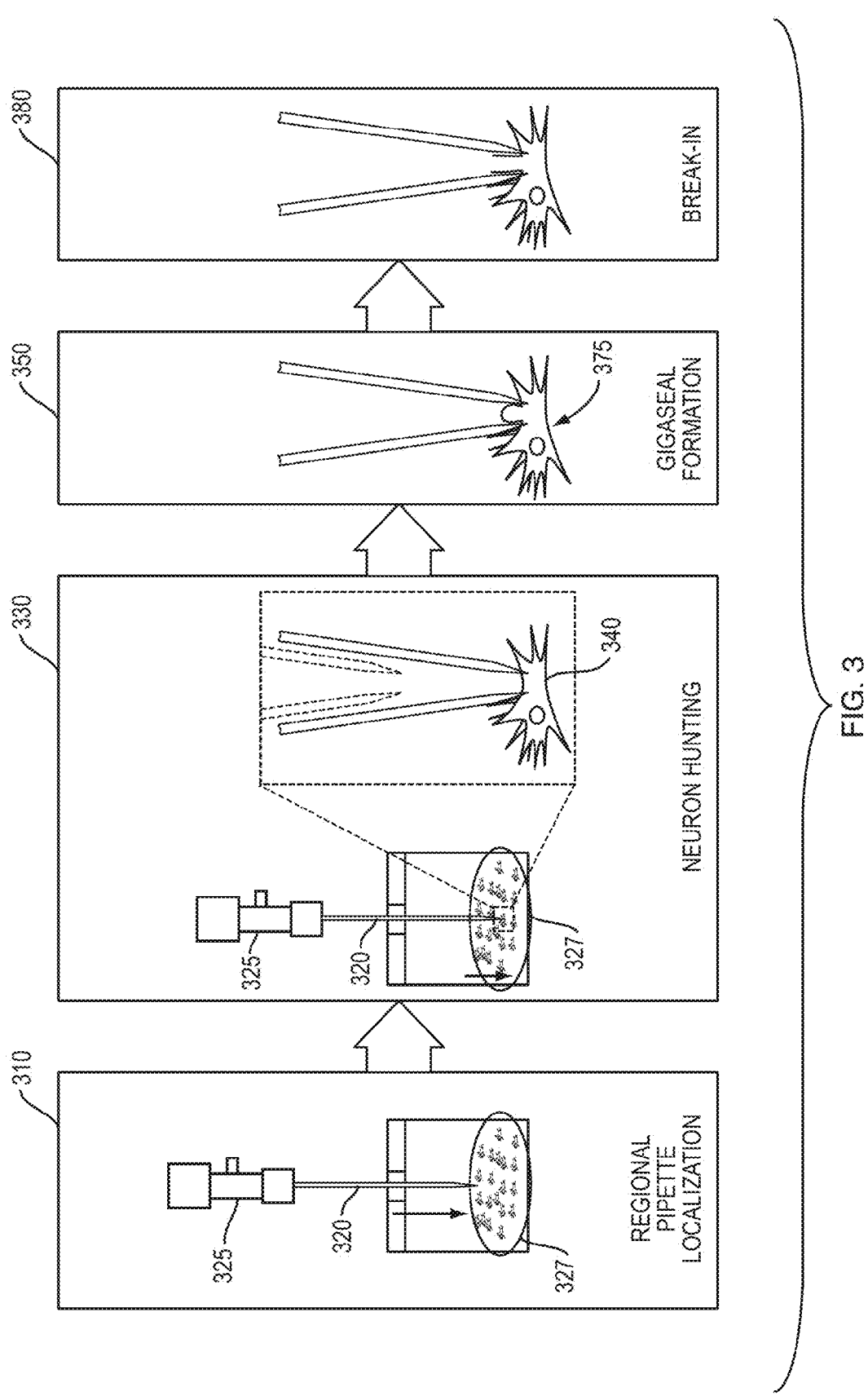
FIG. 3 is a visual depiction of the four stages of the general in vivo patch process for a single cell, carried out using the apparatus and methodology of the present invention.

The different stages of the in vivo multipatching process were optimized by building upon the autopatcher process described in U.S. patent application Ser. No. 13/676,082. FIG. 3 depicts visually the four stages of the general in vivo patch process: regional pipette localization stage 310, during which pipette 320 in holder 325 is lowered to target zone 327 in the brain; neuron hunting stage 330, during which pipette 320 is advanced until neuron 340 is detected via a change in pipette resistance; gigaseal formation stage 350, during which gigaseal cell-attached patch state 375 is achieved; and break-in stage 380, during which the whole cell configuration is achieved.

Figure 4:
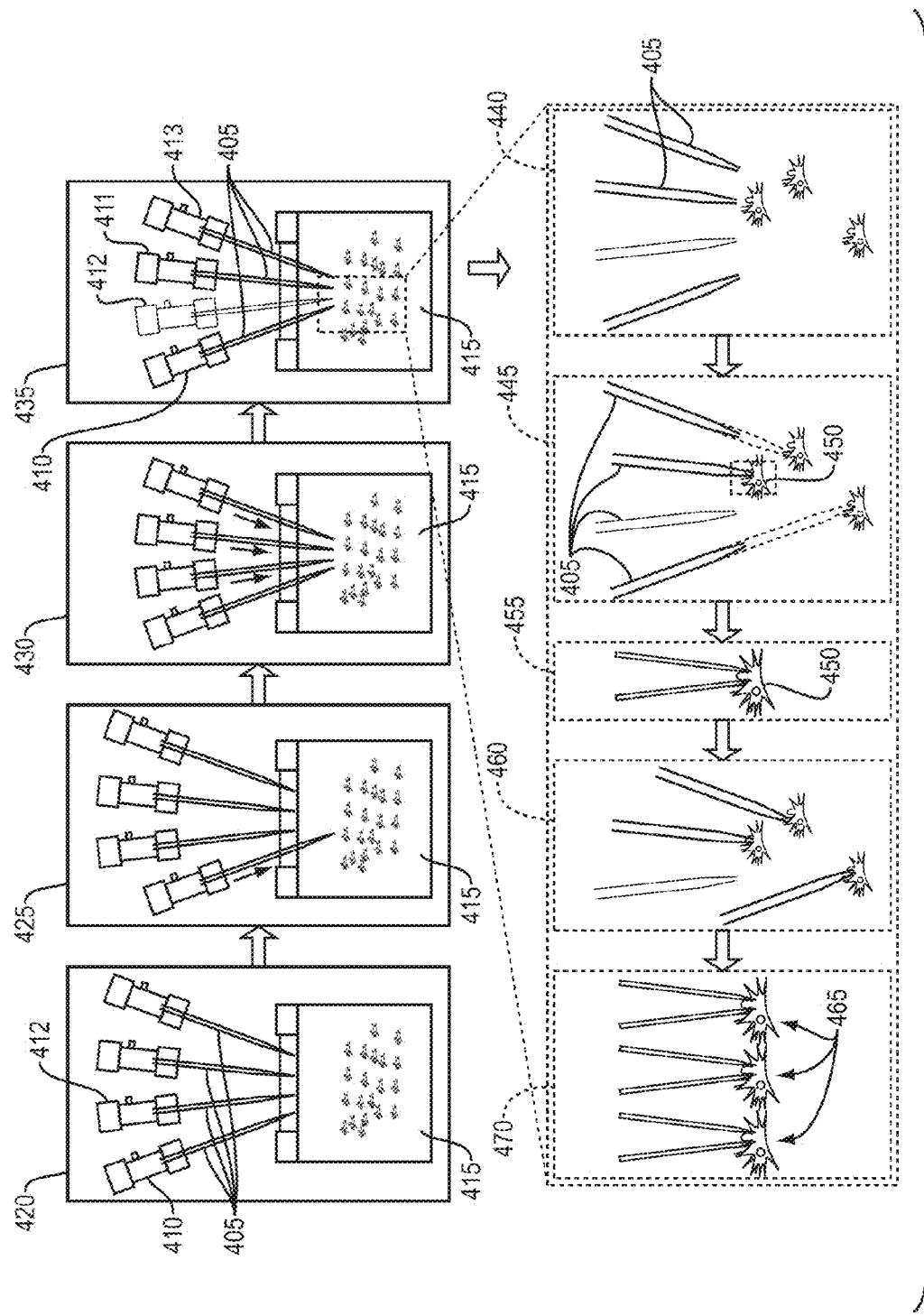
FIG. 4 is a visual depiction of the stages of the in vivo multipatching process for patching multiple cells, carried out using the apparatus and methodology of the present invention.

The process by which the multipatching robot establishes whole cell recordings in multiple neurons is illustrated in FIG. 4 for a 4-channel embodiment. Before the robot is started, pipettes 405 are installed into channels 410, 411, 412, 413 of the multipatcher, and the pressure is set to high positive pressure state in all of them. The pipettes 405 are then positioned in the craniotomy such that their tips enter and probe a brain area 415 within a few hundred micrometers of each other. To begin regional pipette localization, an initial assessment 420 of the pipettes' electrical resistance is carried out to ensure the pipettes are within an acceptable range for patch clamping—typically between 3-9 MΩ. The robot then lowers 425 all the pipettes in a serial fashion to the desired depths set by the experimenter. It is possible to localize different pipettes to different depths within the cortex. Once all the pipettes have been lowered 430, they are checked for tip fouling or blockage. If a pipette 412 has a clogged or fouled tip, the corresponding channel is deactivated 435, and plays no further part in the multipatching process.

Next, the robot enters the "neuron hunting and gigasealing mode", in which the pipettes are advanced in small increments until each detects a neuron via signature changes in pipette resistance, at which time the pipettes stop moving and gigaseal formation is attempted. As shown in FIG. 4, the robot moves 440 all the pipettes in active channels in small incremental steps (2-3 μm), after which it sends 445 a series of predefined square wave voltage pulses (e.g. 10 mV at 10 Hz, with offset voltage set at 0 mV) to the different pipettes, and measures the resultant current traces. This is used to compute the resistance values of the pipettes. This two-step process is repeated while looking for signature trends in resistance traces in one or more channels that indicate suitable contact with a neuron 450 for patch clamping (analogous to the "neuron hunting" stage in the autopatcher operation). After detecting this signature, the robot halts the movement of pipettes in all channels, and attempts to establish 455 a gigaseal in the channels that have encountered a neuron (the "gigasealing" stage in the autopatcher). After a gigasealing attempt has been carried out in a particular channel, its motor is deactivated, and the rest of the pipettes resume neuron hunting. This process is repeated until all the pipettes have encountered neurons and attempted gigasealing 460. At this point, the channels 465 that have successfully formed gigaseals are selected 470 and the robot applied pulses of suction until it successfully breaks into the gigasealed cells (the "synchronized break-in" stage).

The ability of the robot to perform these tasks in an automated and parallel fashion results in a degree of scalability that human operators are not capable of performing manually. Simultaneous, parallel execution of multiple time-point tasks such as lowering multiple pipettes in small increments, monitoring of resistance values in multiple channels, and identification of signature neuron contact trends become increasingly complex tasks for human experimenters and thus become unmanageable to perform manually when the number of pipettes is scaled beyond 2 or 3 channels. Further, automation enables a fine control of the time scales over which different tasks and decisions are executed. For example, it is possible to synchronize events such as breaking into multiple neurons so that the all the gigasealed neurons can obtain whole cell state at the same time, thus enabling the experimenter to maximize the time duration of simultaneous whole cell recordings and normalize the effects of cell dialysis that occur starting from the moment intracellular access is obtained.

Multipatcher robot construction. The multipatcher hardware was assembled using the basic template of the autopatcher robot described in U.S. patent application Ser. No. 13/676,082 and replicating the end actuators four-fold. Modifications were made to the pneumatic systems so that a central pressure control system could be used for independent pressure modulation in all four channels. These are described in detail below.

Figure 5:
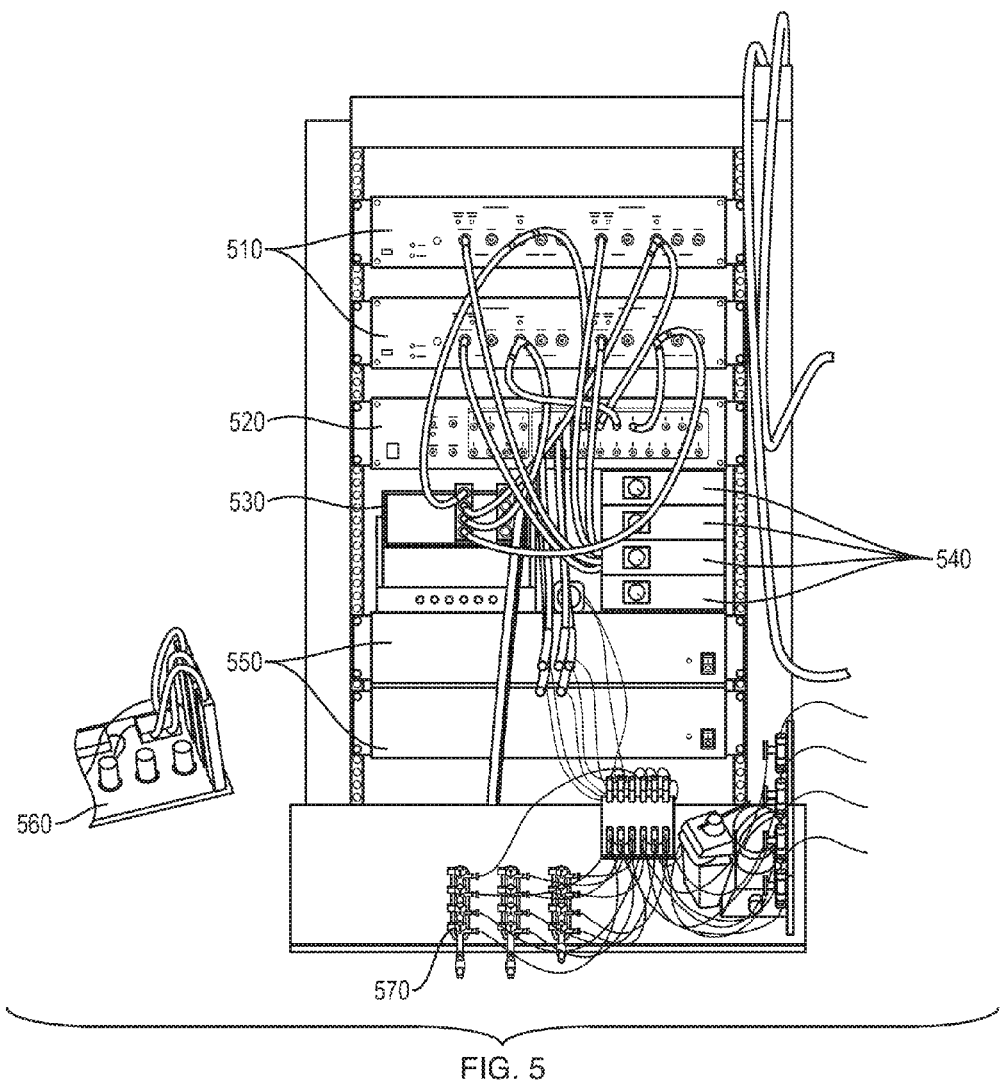
FIG. 5 depicts a prototype implementation of the non-end actuator components of a multipatcher system according to one aspect of the present invention.

FIG. 5 depicts a prototype implementation of the non-end actuator components of a multipatcher system according to one aspect of the present invention. Shown in FIG. 5 are patch amplifiers 510, primary digitizer 520, secondary digitizer 530, switch boxes 540, motor controllers 550, pressure regulator board 560, and pressure switch board 570.

Figure 6:
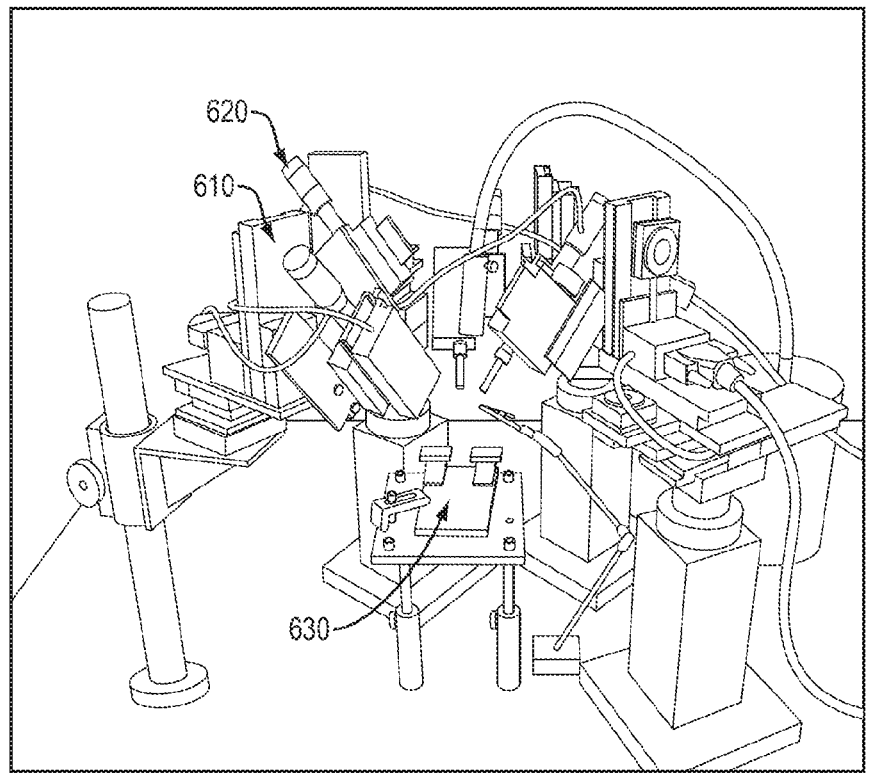
FIG. 6 is a photograph depicting prototype implementations and radial arrangement of four end actuator modules of a multipatcher system according to one aspect of the present invention.

Actuator system. FIG. 6 is a photograph depicting prototype implementations and radial arrangement of four end actuator modules of a multipatcher system according to one aspect of the present invention. The pipette actuator modules are of the same configuration as the single channel system. Briefly, each module comprises a 3-axis linear actuator 610 (MPC285, Sutter Instruments Inc) for holding the patch headstage. For programmable actuation of the pipette in the tilt axis, a programmable linear motor 620 (PZC12, Newport) is mounted onto the 3-axis linear actuator 610. The tilt axis actuator is mounted at an angle of 45 degrees to the vertical. The headstage is in turn mounted on programmable linear motor 620 through a custom mounting plate. The anesthetized mouse is head fixed using custom holder 630, and pipettes are positioned using a stereomicroscope for visualization. Four such actuator modules are placed in close proximity to each other in a radial fashion, forming an asymmetric array for actuating pipettes.

Figure 7:
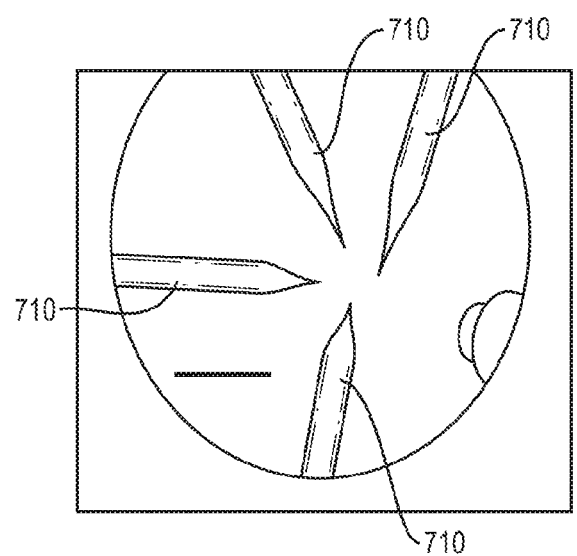
FIG. 7 is a photomicrograph of a set of 4 pipettes tips positioned for targeting the same brain region in an exemplary prototype implementation of the present invention.

FIG. 7 is a photomicrograph of a set of 4 pipette tips 710 from the apparatus of FIG. 6, positioned within a 1 mm square area for targeting the same brain region in the cortex. The scale bar indicates 1.5 mm. In this configuration, it was possible to position four patch pipette tips in an array of 1 mm×1 mm on top of the brain surface. It is desirable to get the pipette tips as close to each other as possible, so as to target neurons within the same microcircuit (<200 µm).

With an angled approach, if the pipettes are lowered into the brain to depths >700 µm, the pipettes can be positioned within a millimeter of each other with this prototype system. Positioning them closer can sometimes result in pipettes colliding with each other during a trial, and was thus not attempted. The programmable linear motors in each of the four channels are connected to a multiplexing switchboard (PZC-SB, Newport; FIGS. 1 and 6). All motors are controlled via a single motor controller (PZC200, Newport Inc). The PZC200 motor controller is in turn connected to the computer through a serial COM port. This architecture allows up to 8 channels to be selected and controlled by the switch box using a single serial port in the computer.

Signal Interfacing with computer. Signals from the headstages ire sent to two 2-channel patch amplifiers (Multiclamp 700B, Molecular Devices) that connect the patch headstages to a computer through a Digidata 1440A analog/digital interface board (Molecular Devices). In a similar fashion to the autopatcher, an additional data acquisition (DAQ) board (cDAQ-9174 chassis with modules NI 9215 for analog inputs and NI 9264 for analog outputs, National Instruments Inc) is connected to the computer via a USB port and to the patch amplifier through BNC cables, for control of patch pipette voltage commands and acquisition of pipette current data during the execution of the multipatcher process. During multipatcher operation, the cDAQ-9174 board sends commands to the patch amplifiers; after acquisition of cell-attached or whole-cell-patched neurons, the patch amplifiers will instead receive commands from the Digidata. A software-controlled co-axial BNC relays (CX230, Tohtsu) is used for driving signal switching between the cDAQ-9174 and the Digidata. The patch amplifier signals are split and streamed simultaneously to the analog input ports of both the cDAQ-9174 and the Digidata throughout and after patching. The multipatcher program is coded in, and runs on, Labview 2011 (National Instruments).

The cDAQ-9174 sampled each channel of patch amplifiers at 15 KHz and without any applied scaling factor, and then filtered the signal using a moving average smoothening filter (half width, 6 samples, with triangular envelope), and the amplitude of the current pulses was measured using the peak-to-peak measurement function of Labview. During gigasealing operations, where currents of the orders of 5-10 pA were measured, an additional exponential filter (decay rate=0.001 seconds) was used to filter out any stray pipette capacitance traces. For resistance measurements, the amplifiers were set in voltage clamp mode using the Multiclamp commander software (Molecular Devices). Square wave of voltage traces were applied: 10 mV in amplitude, at 10 Hz, to the pipettes via the cDAQ-9174 analog outputs. Resistance values were then computed, by dividing applied voltage by the peak-to-peak current observed, for 5 consecutive voltage pulses, and then these 5 values were averaged. During gigasealing and break-in stages of the robot operation, offsets ranging from 0 to −70 mV were applied to the 10 mV, 10 Hz square waveforms to apply the requisite holding potentials needed by the multipatcher process. Multipatched neurons were recorded using Clampex software (Molecular Devices). Signals were acquired at standard rates (e.g., 30-50 KHz), and low-pass filtered (Bessel filter, 10 KHz cutoff). All data was analyzed using Clampfit software (Molecular Devices) and MATLAB (Mathworks).

Figure 8:
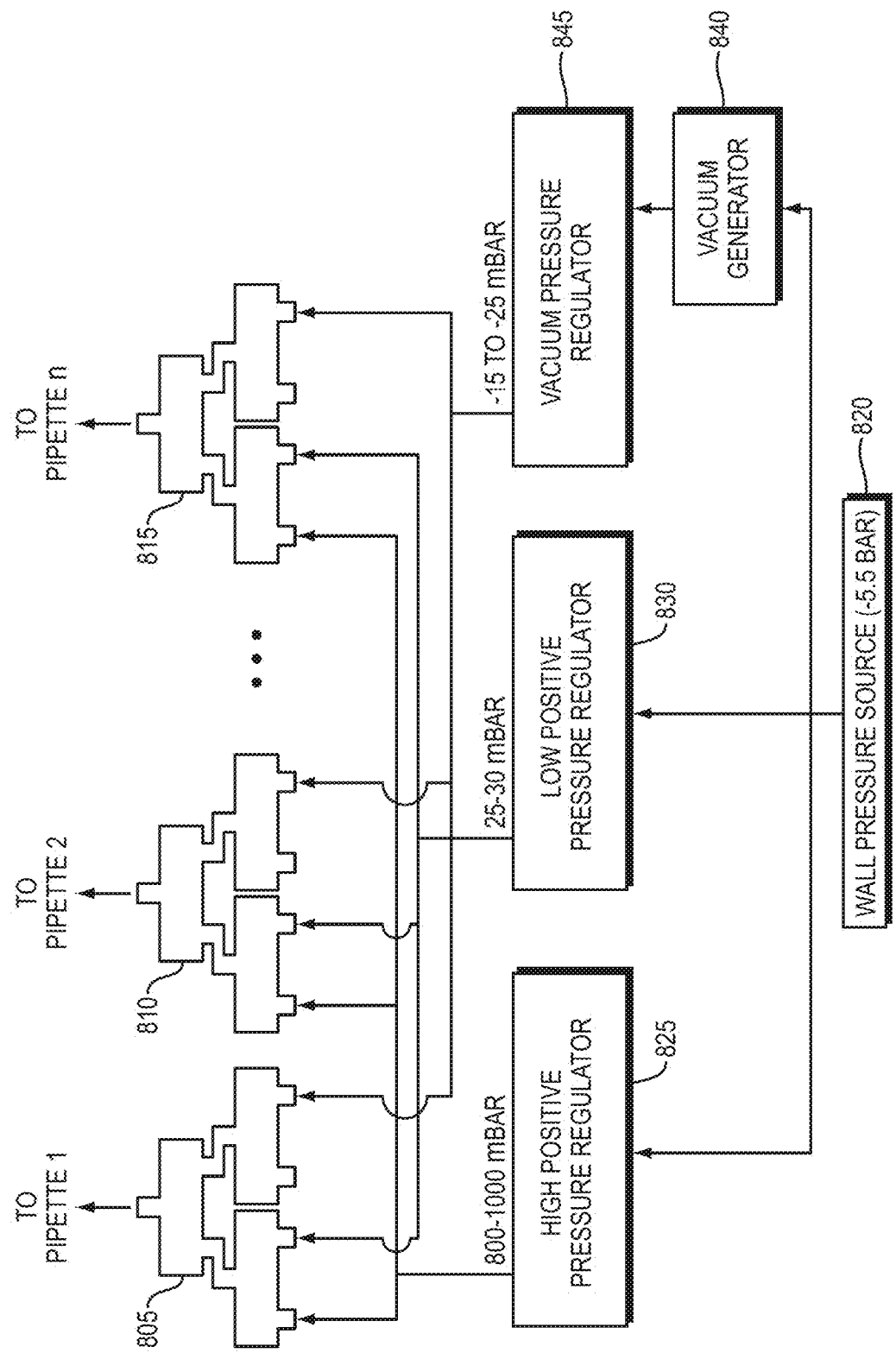
FIG. 8 is a schematic illustration of an exemplary pressure regulator board according to one aspect of the present invention.

Pneumatic system. In a preferred embodiment, the pneumatic system consists of two boards: an analog pressure regulator board (159, FIG. 1) and a pressure switching board (158, FIG. 1). A schematic illustration of an exemplary pressure regulator board is shown in FIG. 8, which depicts the regulation of pressure to different pipettes via valve banks 805, 810, 815 using a common pressure source. It consists of three manual pressure down-regulators (Mcmaster Can) connected to a common wall pressure source 820 outputting a pressure of ~5500 mBar. The wall pressure source is down regulated, or converted to a vacuum pressure, and routed to the designated input ports of the valve switching board. Each valve switching board consists of multiple valve banks (FIG. 2) that can be controlled using the secondary digitizer (FIG. 1) to set a desired pressure state in a pipette. In the exemplary embodiment, the wall pressure is down regulated to three levels, 1 Bar, 100 mBar, and ~500 mBar. The 1 Bar regulated pressure is connected to an electronic pressure regulator 825 (990-005101-015, Parker) for setting to high positive pressure state (i.e. 800-1000 mBar). The 100 mBar regulated pressure is similarly connected a second pressure regulator 830 (990-005101-002, Parker) for setting the low positive pressure state (15-20 mBar). The ~500 mBar regulated pressure source is connected to venturi vacuum generator 840 (AVR038H, Air-Vac), which generates a vacuum pressure of 300 mBar, and that is connected to electronically-controlled vacuum pressure regulator 845 (990-005203-005, Parker).

Figure 9:
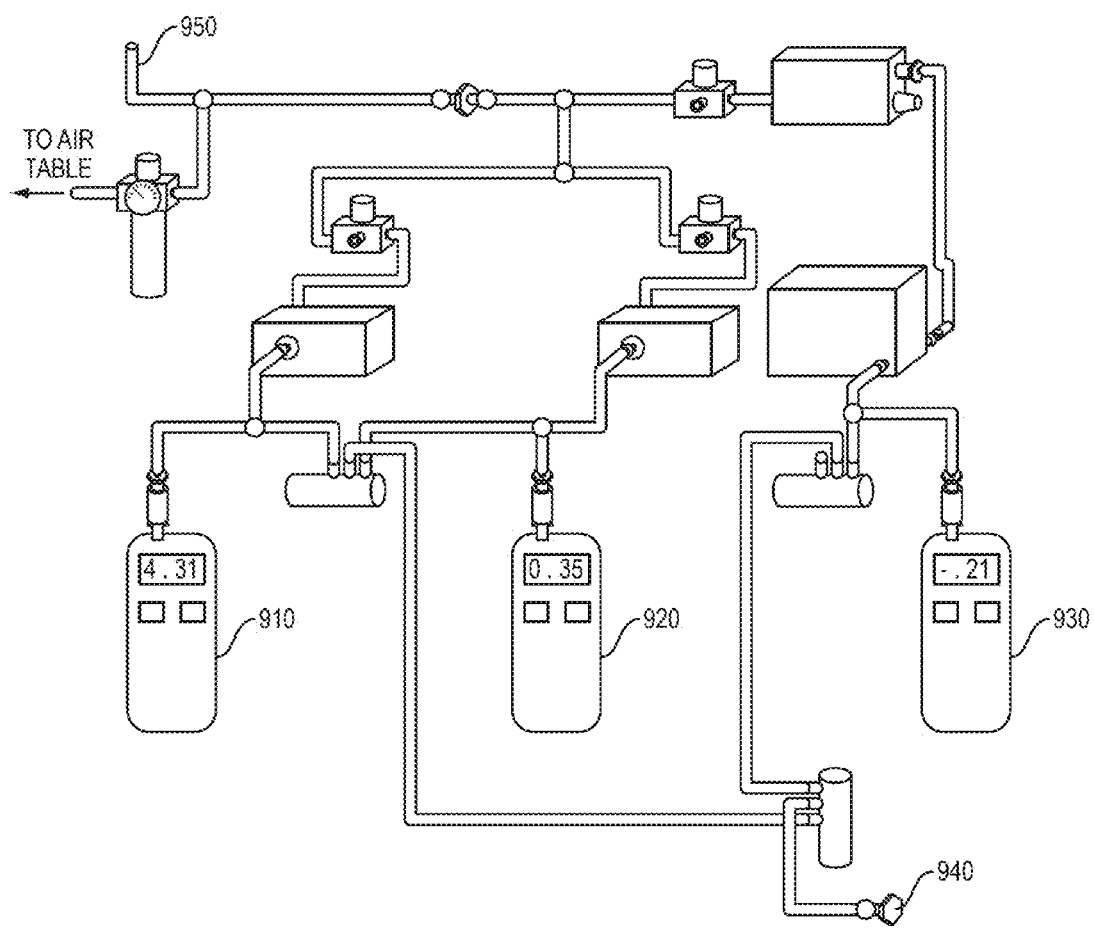
FIG. 9 is a schematic illustration of an exemplary pneumatic system for a single channel according to one aspect of the present invention.

FIG. 9 is an exemplary pneumatic system for a single channel. Shown in FIG. 9 are high positive pressure regulator 910, low positive pressure regulator 920, low vacuum source 930, pressure outlet 940, and pressure inlet 950.

In the prototype embodiment, the pressure outputs of the three electronic pressure regulators were controlled using analog voltages (0-5 V) set manually using potentiometers at 800 mBar (high positive pressure), 20-25 mBar (low positive pressure state), and −15 to −25 mBar (suction state). For breaking-in, the suction pressure was set to vacuum pressures between −150 mBar to −250 mBar. The pressure outputs were measured using digital manometers (4756-FM, Dwyer) and connected to the input manifolds of the pressure switchboard.

The pressure switchboard in the prototype consisted of 4 sets of valve banks, with each valve bank, consisting of 3 solenoid valves (2-input, 1-output, LHDA0533215H-A, Lee Company), as shown in FIG. 2. The input ports in each of the three valves making up the valve bank can be closed or opened using a TTL command from the secondary interface board.

Derivation of a process for multipatching. The process for multipatching in vivo was formulated using the autopatcher process as a basic template and modifying it for parallel control of multiple pipettes. The primary objective of any process used for parallel patch clamping in vivo is to establish whole cell recordings from as many neurons as possible, ideally ensuring arbitrary scalability in a short time period. The simplest implementation of a parallel patch clamping system is to introduce the desired number of fully independent autopatcher units simultaneously into the brain, with the physical constraint being the placement of the pipettes in the desired positions in the brain. Such an independently deployed system would ensure that n number of channels conduct autopatching trials in the same average time as it would take for a single channel autopatcher (5+1 minute).

However, in actual practice this strategy encounters two issues. Firstly, the movement of motors during neuron hunting results in electrical noise, and when coincident with the resistance measurements in other channels, results in errors. Thus, the resistance measurement events in all channels need to be synchronized during the entire process of neuron hunting. Secondly, this approach does not take into consideration the brain tissue displacement caused by the motion of multiple pipettes in the brain. For establishing stable gigaseals, it is critical to prevent any relative motion between the pipette tip and the cell during the gigasealing process. Since encountering a neuron during blind in vivo patch clamping is a random process, in a system with multiple autopatchers running independently, different pipettes encounter neurons at different time points. Movement of pipettes seeking neurons during neuron hunting cause tissue displacement, which hinders the proper establishment of gigaseals in pipettes that have already encountered neurons. Large displacements can also dislodge neurons that are already fully gigasealed onto pipettes. Thus, strategies are required to minimize the amount of tissue displacement during the neuron hunting and gigasealing stages of the process. Other factors considered included hardware and its limitations on parallelization, time and throughput considerations, other physiological factors such as cells dying when exposed to intracellular solution outside, and synchronized gigasealing vs. asynchronous.

Figure 11A:
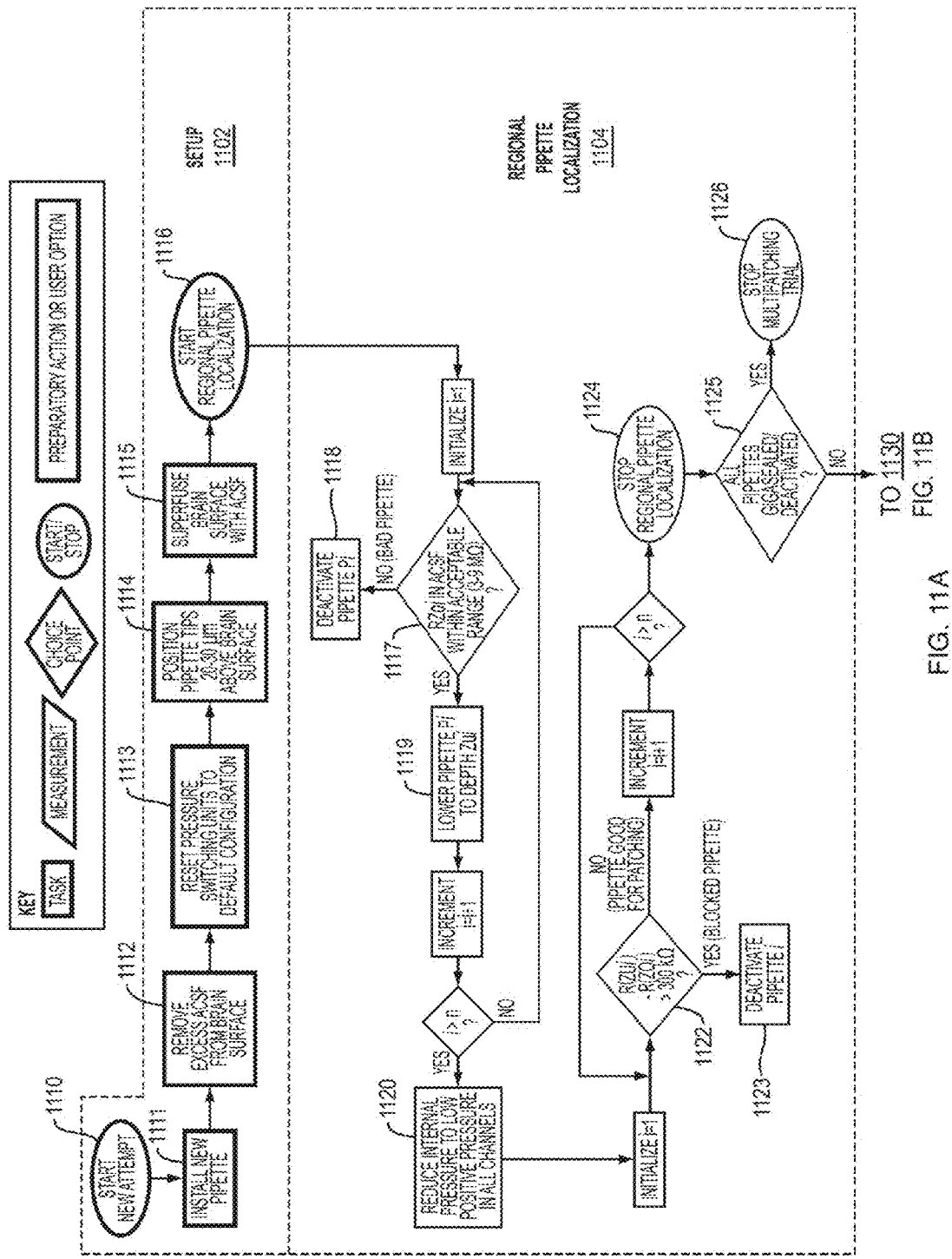
FIGS. 11A-C depict a flowchart showing the steps of a preferred embodiment of the complete generalized automated process for patching multiple neurons in vivo according to one aspect of the invention.
Figure 11B:
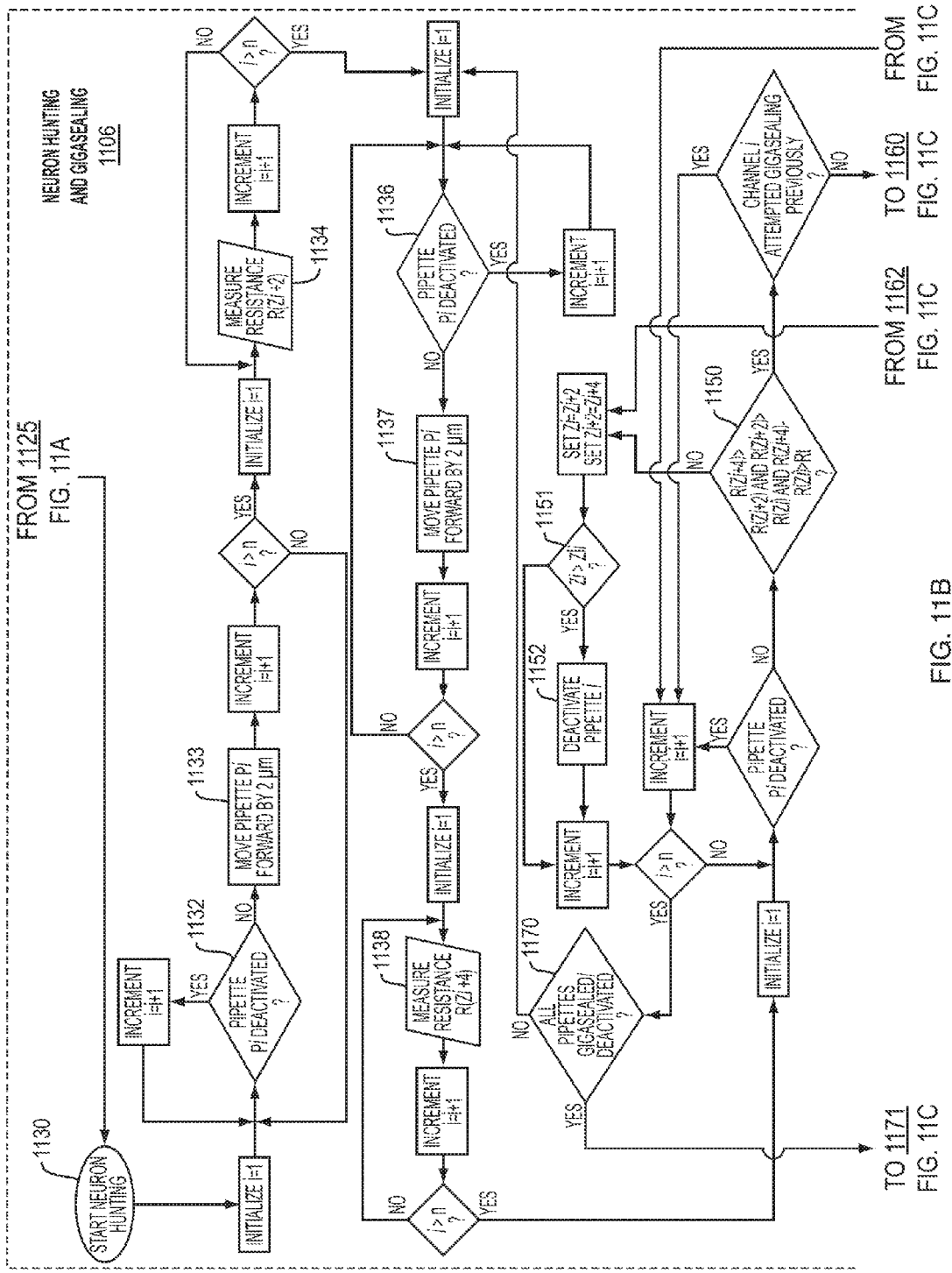
Figure 11C:
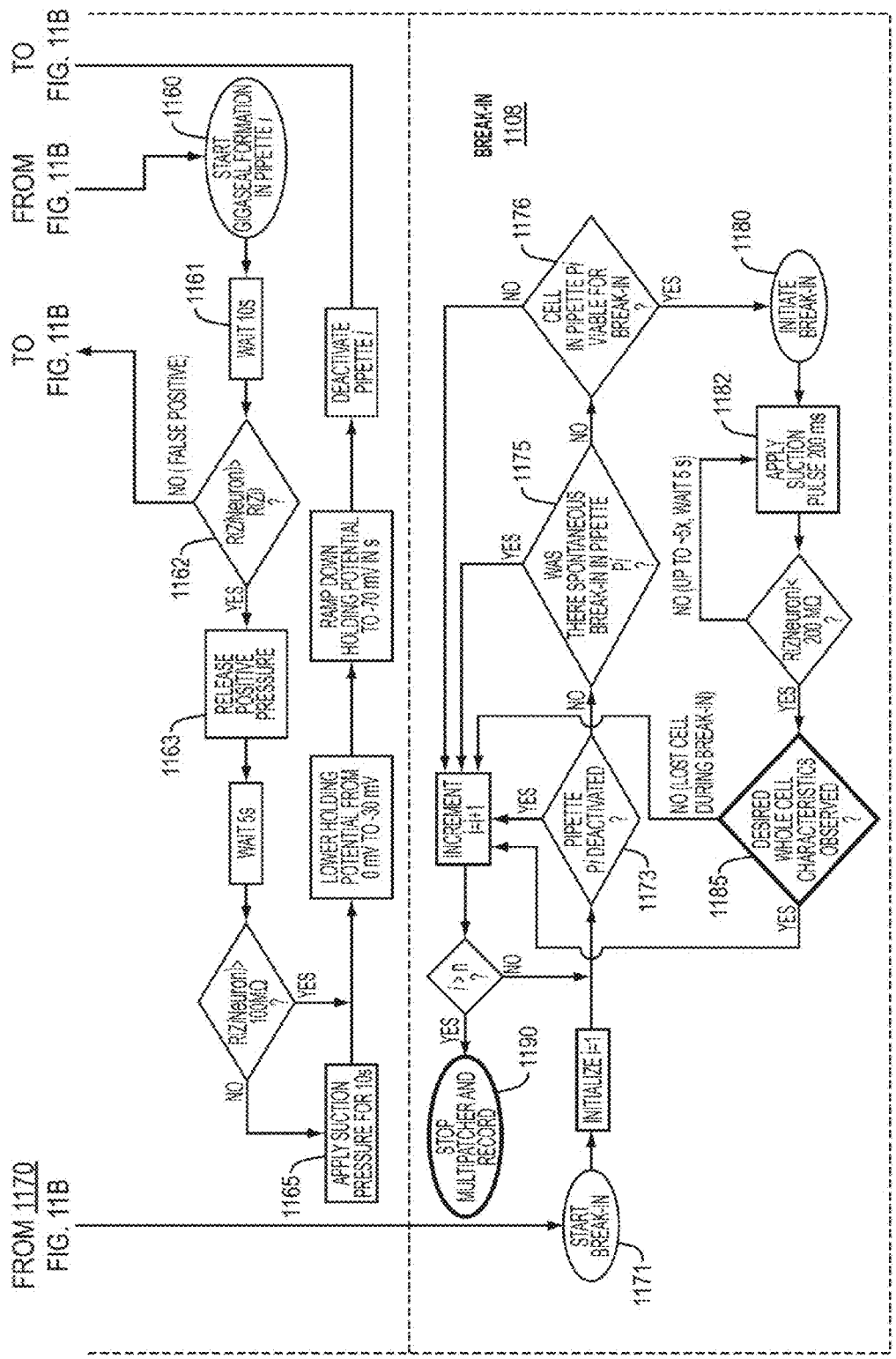

One of the steps taken to mitigate the tissue displacement issue was to perform the regional pipette localization step for all the electrodes in a single step. Thus, each pipette can be lowered to the desired depth, and then neuron hunting in all channels can start simultaneously. This is shown in the "regional pipette localization" section of the flowchart of the preferred embodiment of the multipatcher process (FIGS. 11A-C). Once the pipettes have been installed and positioned in the craniotomies, the multipatcher program is started. At this point the depths for all the pipettes $Z_{0i}$ (i=1, 2, 3 and 4) are denoted as zero by the program. Then the baseline pipette resistances $R_{Z0i}$ in the ACSF or saline bath are recorded. The pipettes are then lowered to the desired depths at a speed of ~200 mm/s. Pipettes in different channels can be lowered to different desired depths, thereby allowing simultaneous recordings from different layers of the cortex, or even different regions of the brain. Once lowered to depth, the pressures in the pipettes are decreased to low positive pressure state (~20-25 mBar) and the pipette resistances $R_{ZUi}$ assessed for a second time. The values of $R_{ZUi}$ and $R_{Z0i}$ are compared and if resistance increases greater than 0.35 MΩ are detected in any of the channels, the pipette tips are deemed blocked or fouled, and those channels are deactivated and play no further part in the multipatcher trial. If all pipettes are found to be inadequate for patching, the program stops, and a new trial has to be started. It was found that pipettes got fouled at a rate of 18.2% (n=28 out of 156 pipettes in 39 trials), which is comparable to the rate of pipette blockage in the autopatcher. By lowering all the pipettes into the regions of interest in a single step, large macroscopic displacements of pipettes (and the corresponding tissue displacement) are eliminated. This completes the "regional pipette localization" stage of the multipatcher process. The multipatcher next seeks out neurons to gigaseal and break-in to in order to establish whole cell recordings.

Two factors needed to be taken into consideration while formulating methodologiess for the subsequent stages of patch clamping. Firstly, it is advantageous to perform all the steps of neuron hunting, gigasealing, and break-in in a parallel manner, so as to reduce the time duration of the experiment. Secondly, as the number of channels is scaled up, the supporting hardware required for independent pressure control scales up proportionally. Each channel of the multipatcher requires three solenoid valves and three corresponding TTL control channels. Thus, for n number of channels, this number would be 3n. When dealing with large number of channels (>50), it becomes impractical to have independent control over the pressures for each individual channel. One way to simplify this requirement is to synchronize the gigasealing events for all the channels. In this way, the pressures of all the systems can be switched between different states at the same time, i.e. from low positive to atmospheric pressure, followed by suction application using just one set of solenoid switch valves.

Figure 10A:
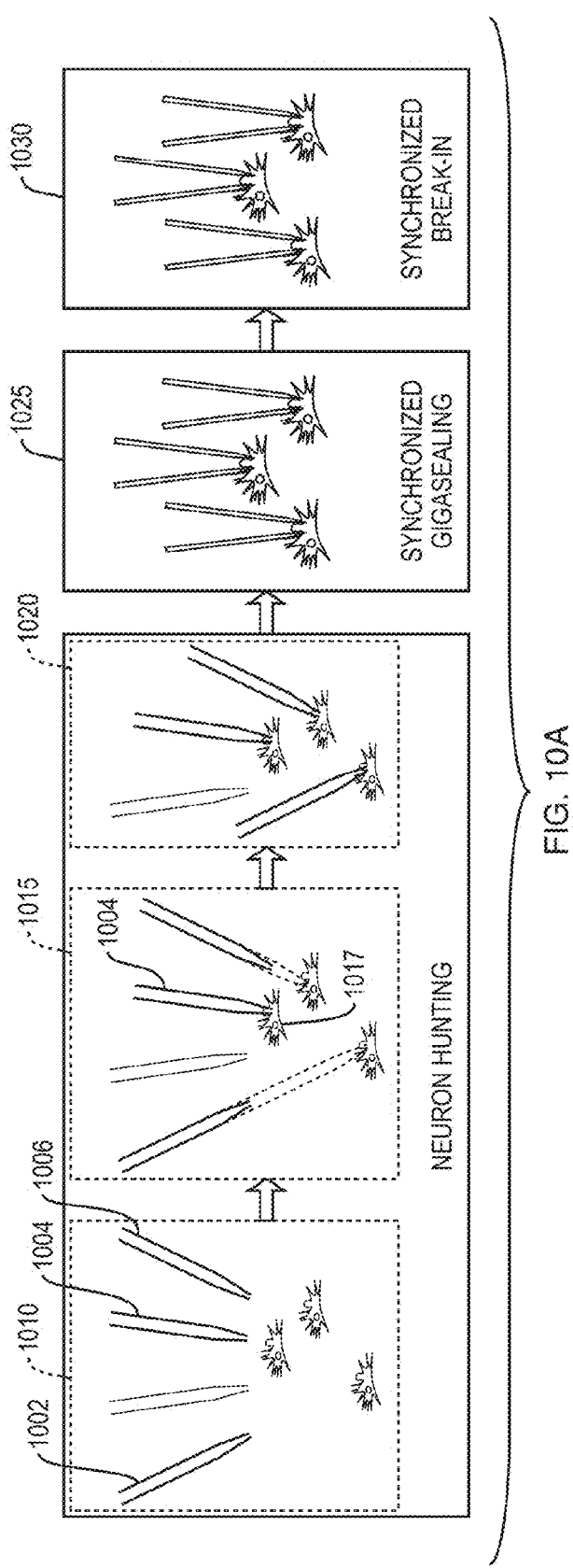
Figure 10C:
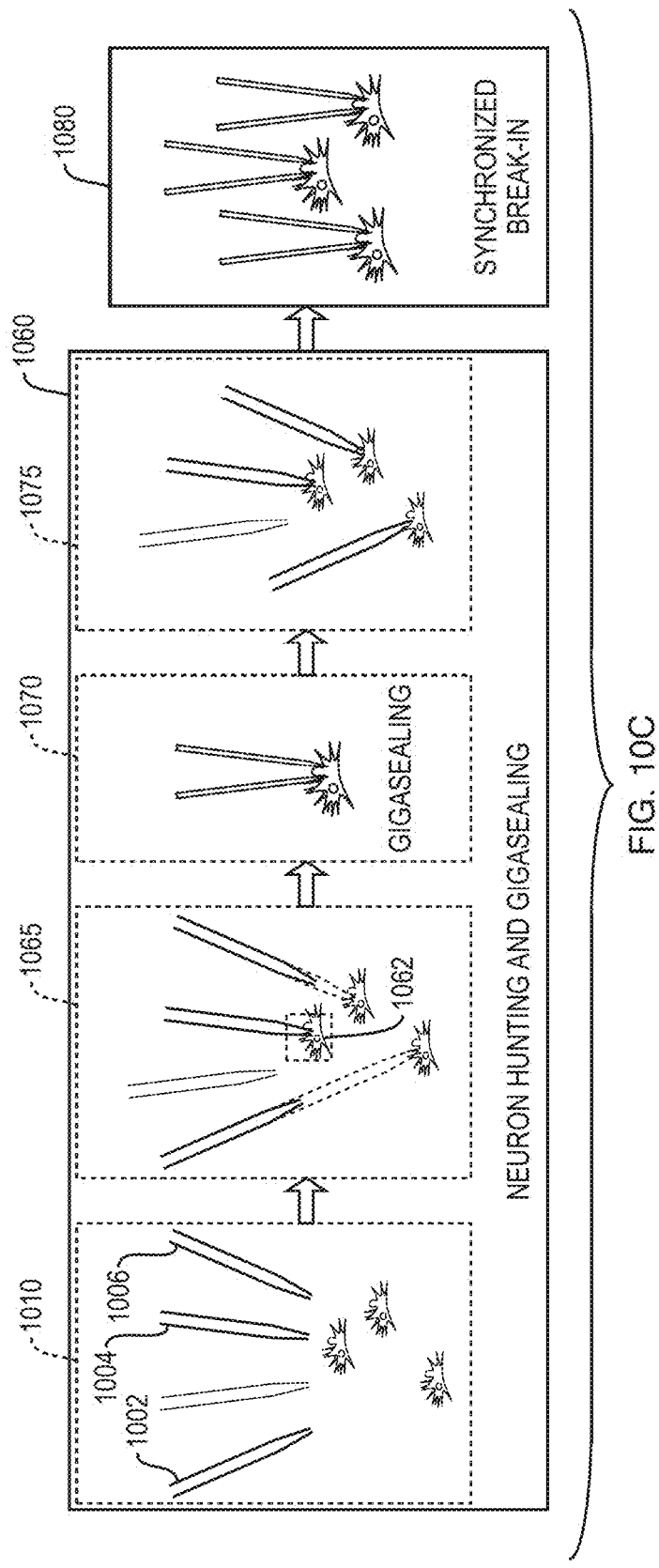

Different means to achieve the end whole cell state in all pipettes in as synchronized a manner as possible were explored. FIGS. 10A-C are visual depictions of the stages of three different embodiments of the in vivo multipatching process carried out using the apparatus and methodology of the present invention. In the methods depicted in FIGS. 10A and 10B, all cells reached gigasealed state synchronously, while in FIG. 10C, only the break-in stage was synchronized. In FIG. 10A, each pipette stops when neurons are encountered, in FIG. 10B the pipettes are retracted back by a fixed distance after contact, and in FIG. 10C pipettes attempt gigasealing immediately upon encountering neurons. In FIGS. 10A-C, pipettes that are depicted as faded represent those that were deactivated at the end of the regional pipette localization stage and play no part in the process.

A simple extension of the autopatcher process is shown in FIG. 10A. The active pipettes 1002, 1004, 1006 are first actuated 1010 in steps of 2 µm, followed by an assessment of their pipette resistances. This process is repeated iteratively, until one or more pipettes encounters 1015 a neuron 1017, as detected by the criterion used by the autopatcher, i.e. monotonic increase in pipette resistance greater than 250 kΩ over two consecutive actuation steps. Once a neuron 1017 is detected 1015, the corresponding motor is simply deactivated and the rest of the pipettes 1002, 1006 continue the process of neuron hunting, until all pipettes encounter neurons and stop 1020. At this time, the pressure in all pipettes 1002, 1004, 1006 is simultaneously released and gigasealing is attempted 1025, in a manner identical to the autopatcher, followed by synchronized break-in 1030. This process is very similar to that employed by the autopatcher, but required a wait before the release of positive pressure in order to permit gigasealing in all of the channels.

In 19 trials using the method of FIG. 10A (in n=3 mice), where three or more active pipettes performed the neuron hunting and gigasealing tasks, the multipatcher established successful gigaseals 22% of the time (15 out of a total of 68 attempts in 19 trials, with 8 out of 76 pipettes having been deactivated at the end of regional pipette localization stage due to tip blockage). The pipettes reaching neurons last, and thereby immediately going into gigasealing, successfully formed gigaseals 36.8% of the time (7 out of 19 attempts). In the rest of attempts, successful gigaseals were formed 16.3% of the time (8 out of a possible 49 attempts). This number is significantly lower that what was previously found using the autopatcher. The resistance traces in this second set were analyzed, and it was found that, in some of the traces, the resistance values decreased to the baseline readings obtained before contact with a neuron during the course of waiting for pipettes in other channels (20% of the time, 10 out of 49 trials). This indicates that the tissue displacements caused by the motion of other pipettes in the brain was large enough to dislodge neurons from the optimum relative positions with respect to the neurons for gigasealing. Further, only 20.5% (8 out of the remaining 39) of the pipettes established successful gigaseals, even when elevated resistance readings (indicating contact with a neuron) were observed. It was hypothesized that the constant exposure of the neurons to the intracellular pipette solution ejected out of the pipette, while waiting for the rest of the channels to find neurons, possibly had a deleterious effect on the neurons and resulted in lower rates of gigasealing.

To mitigate this effect, a second method, shown in FIG. 10B, was implemented. In this procedure, the multipatcher proceeds along the same lines as the method of FIG. 10A, with the active pipettes 1002, 1004, 1006 being actuated 1010 in steps of 2 µm, followed by an assessment of their pipette resistances, until a neuron 1035 is encountered at one of the channels, at which time, the pipette is retracted by 30 µm and stopped 1040. A value of 30 µm was chosen because that was the minimum distance the pipettes needed to be refracted before the resistance measurement decreased to the average baseline value (n=15 trials). This positions the tip at a distance where the ejection of the intracellular solution has no effect. This process is repeated for all the active pipettes, so that at the end of neuron hunting 1045, the relative positions of all the pipettes, and the corresponding neurons they encountered are the same (~30 µm, after accounting for tissue displacement). As a final neuron-hunting step, all pipettes are moved forward 1045 by the same distance (30 µm), and gigasealing is attempted synchronously 1050, followed by synchronized break-in 1055.

The method of FIG. 10B yielded a success rate for gigasealing of ~20% (12 out of 59 attempts in 17 trials, with 9 pipettes deactivated at the end of regional pipette localization stage due to tip blockage). Again, this was much less than what would be expected when using the autopatcher process. The resistance measurement traces for this method were analyzed, and it was found that, after the final neuron hunting step when all pipettes advanced forward by 30 µm, resistances went back to the elevated values indicated by contact with neurons in only 45.7% (27/59 attempts), again indicating that tissue displacement effects were in play.

As has been observed previously, once gigasealed cell attached or whole cell stage has been achieved, the configuration is remarkably stable against motion artifacts. This has been used previously to record in the whole cell state from head fixed, freely moving animals. Several groups have also shown that it is possible to carry out loose cell attached recordings for tens of minutes to hours. Further, from whole cell stage, pipettes can be retracted for up to 50-60 µm before an outside out patch is established. Using this property, a third method was implemented wherein, as shown in FIG. 10C, once a pipette encounters a neuron, the program pauses neuron hunting in all channels and attempts gigasealing in the channel that has encountered a neuron.

As shown in FIG. 10C, in this method, once the robot enters the neuron hunting and gigasealing stage 1060, it lowers 1010 pipettes 1002, 1004, 1006 in the active channels by 2 µm in a serial fashion, followed by an assessment of the pipette resistances, until a neuron 1062 is encountered at one of the channels. These two tasks are performed repetitively, while constantly looking for time-series trends in resistance measurements that are indicative of contact with a neuron. These trends are typically monotonic increases in pipette resistance over 0.2-0.25 MΩ within three measurements. Whenever a channel positively encounters a neuron 1062, pipette actuation in all channels is stopped and gigasealing protocol 1070 is initiated.

The multipatcher waits 10 seconds to see if the pipette resistance decays back to baseline value. If it does, the program restarts neuron hunting 1010. Otherwise, the program releases positive pressure in the pipette, waits 5 seconds, and applies suction pressure for 10 seconds. Once the suction pressure is released, the holding potential is stepped down to −30 mV, and ramped down from that value to −70 mV over the next 30 seconds. This completes the "gigasealing" attempt for that pipette. Once the gigasealing protocol 1070 is completed in a particular channel, the neuron is held at a holding potential of −70 mV, the motor is deactivated and neuron hunting is re-started 1010 in the remaining active channels. This process is repeated until all the active channels have encountered neurons and undergone gigasealing 1075, following which synchronized break-in 1080 is attempted.

FIGS. 11A-C together comprise a flowchart showing the steps of a preferred embodiment of the complete generalized automated process for patching multiple neurons in vivo according to one aspect of the invention, including strategies for stage execution, and quantitative milestones governing process flow and decision making There are four stages of the process, Setup 1002, Regional pipette localization 1104, Neuron hunting and Gigasealing 1104, and Break-in 1108, and within each stage the symbols depicted in FIGS. 11A-C represent tasks, measurements, and choice points. Abbreviations used in the steps depicted in FIGS. 11A-C include: ACSF, artificial cerebrospinal fluid; $RZ0_i$, resistance of pipette i at depth Z in the brain, in microns (with the z-axis pointing downward, e.g. larger values of Z indicate deeper targets); upper depth limit of the region targeted by the regional pipette localization stage; Zl, lower depth limit of the region targeted by the regional pipette localization stage of each pipette i; $R(Z_{iNeuron})$, pipette resistance at the depth at which the neuron is being recorded (which will vary over time, as the later stages of the process, gigasealing and breaking-in, occur); and Rt, pipette resistance threshold for neuron detection. The blocks shown in Setup 1102 are manual tasks that are carried out by the experimenter, while the remaining blocks are executed by a computer.

In FIGS. 11A-C, during setup stage 1102, for each new attempt 1110, pipettes are placed 1111 in the holder, excess artificial cerebrospinal fluid (ACSF) may be removed 1112 from the brain surface, and pressure switching units are reset to the default configuration 1113. Pipette tips are positioned 1114 above the brain surface, the brain surface is superfused 1115 with ACSF, and regional pipette localization 1104 is initiated 1116. During regional pipette localization stage 1104, pipette resistances are checked 1117 and bad pipettes are deactivated 1118. For the remaining pipettes, the robot lowers 1119 the pipettes at a speed of 200 μm/s to the appropriate depth for neuron hunting and then reduces 1120 the internal valve pressure to low positive pressure for all channels. Pipettes are then assessed for blockages 1122, with blocked pipettes being deactivated 1123. Regional pipette localization is ended 1124, and if all pipettes have been either gigasealed or deactivated 1125, the trial is stopped 1126.

During neuron hunting and gigasealing stage 1106, neuron hunting is initiated 1130. The robot checks a pipette for deactivation 1132, and if it is not deactivated, the robot iteratively moves 1133 the pipette and measures 1134 the resistance in order to determine whether or not a neuron has been encountered. This is repeated until all pipettes have been moved 1133 and checked 1134. This process is iteratively repeated, checking pipettes for deactivation 1136, moving them 1137, and checking 1138 for neuron encounters. If, as determined 1150 by a time series of resistance measurements, no neuron has been encountered after the pipette distance has been repeatedly adjusted for a pipette and the maximum probe depth has been reached 1151, the pipette is deactivated 1152. If, as determined by the resistance measurements, a neuron has been encountered for a particular pipette, gigaseal formation is initiated 1160 for that pipette, after a pause 1161 to check 1162 for false positives, starting with release 1163 of positive pressure on the pipette and, if necessary, application 1165 of suction pressure. This process is continued until gigaseal formation or deactivation has occurred for all pipettes. Once gigaseal formation is achieved and verified for all active pipettes 1170, break-in stage 1108 is initiated 1171. During this stage, pipettes are checked for deactivation 1173, and active pipettes are checked for spontaneous break-in 1175. Those pipettes without spontaneous break-in are checked for viable cells 1176, and for those with viable cells break-in is initiated 1180 by application 1182 of suction, leading hopefully to a successful whole cell patch clamp 1185. When break-in has been attempted or achieved for all pipettes with viable cells, the multipatcher process is completed 1190.

Performance of the multipatching robot. The performance of a 4-channel multipatching robot was validated in the cortex of anesthetized mice. The multipatcher, running the process shown in FIGS. 4 and 11A-C, obtained successful whole cell recordings in 1 or more channels 58.9% of the time (n=23 out of 39 trials, n=7 mice). Success was defined as being able to hold a cell in current clamp mode with under 500 pA of injected current for at least 5 minutes. Out of these 23 trials, the multipatcher successfully recorded from pairs of neurons in 11 trials and from a triplet of neurons in one trial. Thus overall, the multipatcher was able to establish successful whole cell recordings from multiple neurons 30.76% of the time (12 out of 39 attempts). The ability to record from pairs and triplets of cells simultaneously demonstrates the scalability of the multipatching robot process; by increasing the number of controllable pipettes, even higher numbers of simultaneous whole cell recordings can be obtained. In these trials, overall, 17.9% of the pipettes got blocked (n=28 of 156 pipettes in n=39 trials), a percentage that is comparable to those obtained when using the single channel autopatcher. The entire multipatcher trial, from start of regional pipette localization to end of break-in, took an average of 10.45+2.56 minutes. Thus, per channel, the multipatcher requires 2.61+0.64 minutes, which is again comparable to the time taken by the single channel autopatcher to establish whole cell recordings.

When the multipatcher attempts break-in, the user can choose the channels in which break-in needs to be executed. An iterative method was used wherein the duration of the suction pulses and the applied pressures were incremented in each successive attempt, until a successful break-in was formed. Table 1 reports pressure and time setting for iteratively achieving successful break in, while causing as minimal perturbation to the cell as possible.

TABLE 1

|  | 200 ms | 250 ms | 300 ms | 350 ms | 400 ms | 450 ms | 500 ms | 750 ms | 1000 ms |
| --- | --- | --- | --- | --- | --- | --- | --- | --- | --- |
| 150 KPa | Attempt 1 | Attempt 2 | Attempt 3 | Attempt 4 | Attempt 5 | Attempt 6 | Attempt 21 | Attempt 22 | Attempt 23 |
| 200 KPa | Attempt 7 | Attempt 8 | Attempt 9 | Attempt 10 | Attempt 11 | — | Attempt 24 | Attempt 25 | Attempt 26 |
| 250 KPa | Attempt 12 | Attempt 13 | Attempt 14 | Attempt 15 | Attempt 16 | — | — | — | — |
| 300 KPa | Attempt 17 | Attempt 18 | Attempt 19 | Attempt 20 | — | — | — | — | — |

Using this process, successful gigasealed cell attached recordings were obtained from 35.93% of the active pipettes (46 out of 128 pipettes in 39 trials, 28 pipettes were deactivated at the end of the regional pipette localization stage). This was the highest yield obtained from all three iterations and was thus used as the final generalized process (shown in flowchart form in FIGS. 11A-C). Of the 46 neurons that were gigasealed, successful whole cell recordings were established in 36 neurons, achieving a break-in success rate of 78.2%. Successful whole cell recordings from multiple neurons, i.e. 2 or 3, were established in 30.7% (12 out of the 39 trials, with 11 recordings where pairs of neurons were connected, and 1 recording where a triplet of neurons were recorded) of the trials, but whole cell recordings in all 4 pipettes were not achieved in any of the trials. While the process was formulated and tested using a 4-channel multipatcher system, it will be clear to one of skill in the art that the methodology and apparatus of the invention can be applied to control arrays of arbitrarily large number of pipettes. More pipettes would ensure, higher success rate of obtaining multiple patch recordings.

Figure 12:
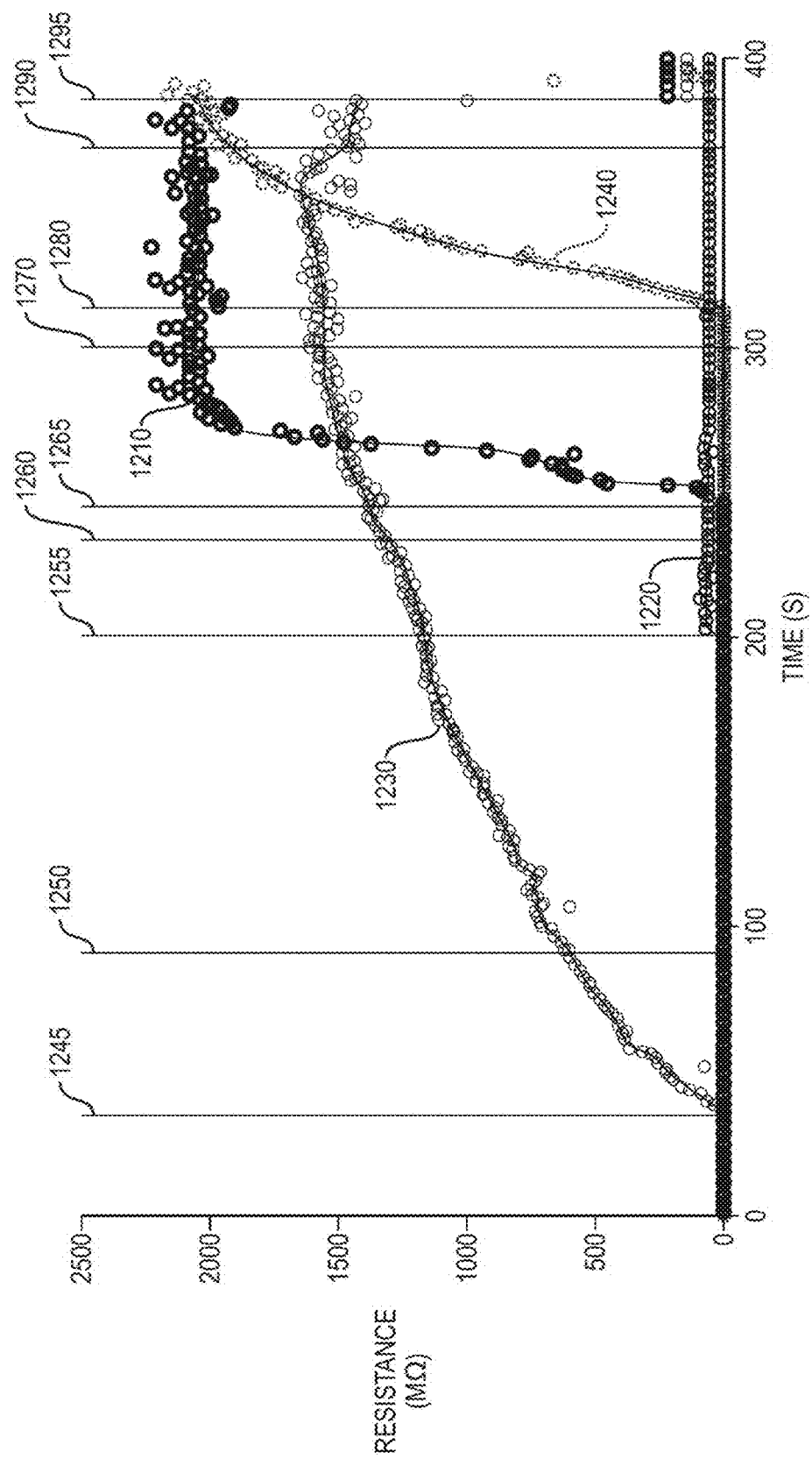
FIG. 12 is a graph of representative traces of pipette resistances recorded by the prototype multipatcher during a successful multipatcher trial.

Time course of Multipatcher operation. A representative trace of resistance readings recorded from the four channels of the multipatcher during a full trial is shown in the graph in FIG. 12. The resistance traces are shown for channels 1 (1210), 2 (1220), 3 (1230), and 4 (1240). The key events during the trial are denoted by time dividing lines 1245, 1250, 1255, 1260, 1265, 1270, 1275, 1280, 1285, 1290, 1295. The detection of a neuron by channel 3 1230 is shown at time 1245. Between time 1245 and time 1250, all pipettes paused neuron hunting and stopped advancing, and gigasealing was attempted in channel 3 1230. The gigasealing tasks were carried out as previously described at time 1250, set at −70 mV. The entire gigasealing process was programmed to execute in 60 seconds. At the end of 60 seconds, channel 3's motor was deactivated and the holding potential held at −70 mV, as the rest of the channels resumed neuron hunting. At time 1255, the robot detected contact with a neuron in channel 2 1220. The same gigasealing steps described previously for channel 3 1230 were used for channel 2 1220 between times 1255 and 1260, resulting in an unsuccessful gigaseal formation. It must be noted that gigasealing was attempted only for 35 seconds, as opposed to the full 60 second routine. Because it was clear that the cell would not gigaseal, the experimenter terminated the gigasealing attempt using a manual intervention mechanism in the software interface. At time 1260, channel 2's motor was deactivated, at the end of which the holding potential was held at −70 mV, while channels 1 1210 and 4 1240 resumed neuron hunting. Between time 1265 and time 1270, the robot paused again, to successfully attempt a gigaseal formation in channel 1 1210. Finally, the same sequence of events was applied to channel 4 1240, and a successful gigaseal resulted between time 1280 and time 1290. At time 1295, the gigasealed neurons attached to the patch electrodes in channels 1 1210, 3 1230, and 4 1240 were broken into to establish whole cell patch recordings.

An important distinction from the autopatcher process is to be noted. The time for execution of gigasealing tasks was fixed at 60 seconds, whereas in the autopatcher, break-in was initiated at the discretion of the experimenters. Thus, average gigasealing time reported for the autopatcher is higher than 60 seconds. The gigasealing times recorded for autopatching are the times taken for gigaseals to fully stabilize and asymptote, upon which break-in was initiated by the experimenter. In the multipatcher process, a fixed time was employed for gigasealing with the cell being clamped at −70 mV holding potential at the end of the 60-second gigasealing process. Thus, even as the program resumed neuron hunting with pipettes that were yet to encounter neurons, the gigasealed cell's or cells' seal resistance continued to increase and finally asymptote due to the hyperpolarizing holding potential that was applied. This did not, however, apply to the channel that attempted gigasealing last, for which the usual conditions used for autopatching were applied.

In a subset of the trials, the time taken to fill, install, and position the pipettes in a multipatching trial was measured. For four channels, the average time taken for filling and installing pipettes was 12.48+1.36 minutes (n=18 trials), and the time taken for the completion of multipatcher trials culminating in successful whole cell recordings of one of more neurons was 10.45+2.56 minutes (n=14 trials). Thus, for a single channel, it takes 3.2+0.31 minutes for pipette installation, and 2.61±0.64 minutes for whole cell patch clamping, as compared to the autopatcher, which requires 2.0±0.4 minutes for pipette installation and 5±2 minutes for operation. The increased time for pipette installation per channel is due to the increased complexity of tasks involved in positioning the pipettes in close confinement. However, this is offset somewhat by the reduced time for operation/ channel, mainly due to limiting the gigasealing operations of all but one channel to 60 seconds.

If the current system were to be scaled up for controlling higher numbers of pipettes, it is expected that installation and robot operation times would scale up proportionally, with the time for installation increasing more rapidly. Thus scaling up beyond 10-12 channels would benefit from a redesign of the actuation modules in order to enable quick replacement of pipettes for high-throughput operation.

Quality of patch recordings. Representative voltage traces recorded simultaneously from a triplet of neurons in current clamp mode that were simultaneously whole cell recorded using the multipatcher are shown in FIG. 13A. The three neurons were targeted in the motor cortex, ~700 micrometers from each other. Mean resting potentials for the neurons were −55.93+7.21 mV (top 1310), −60.3+4.52 mV (center 1320) and −69.23+4.58 mV (bottom 1330). As observed previously with the autopatcher, a majority of the neurons exhibited up and down states, typical of cortical neurons under anesthesia. The up and down states in all neurons were highly correlated, as can be seen in FIG. 13B, which is a detail view of sub-threshold membrane potential fluctuations during the time highlighted by dashed box 1340 in FIG. 13A. Neurons recorded displayed a high degree of correlation in the up and down state fluctuations. Spikes in this time period have been truncated for better visualization.

Figure 14C:
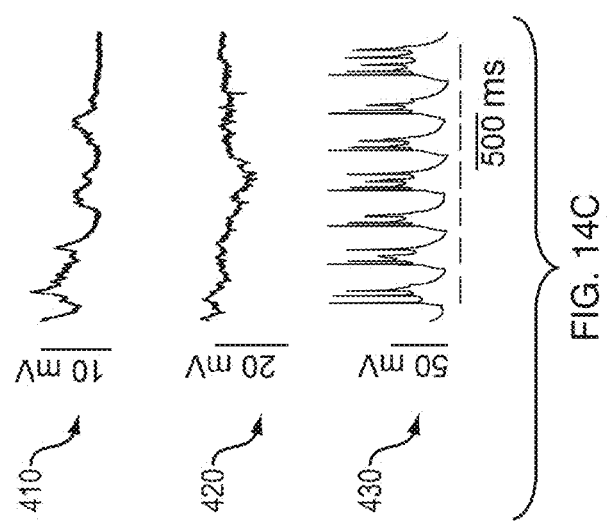
FIGS. 14A-C are current traces showing the results of investigation of synaptic connectivity between whole cell patched neurons using the neurons recorded in FIGS. 13A-B.
Figure 14B:
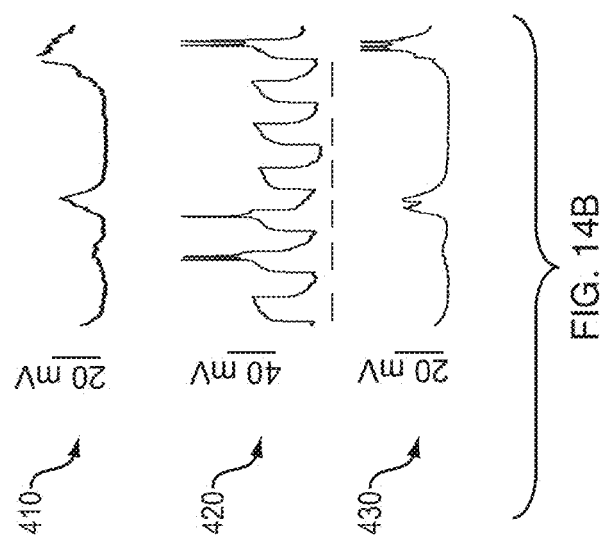
Figure 14A:
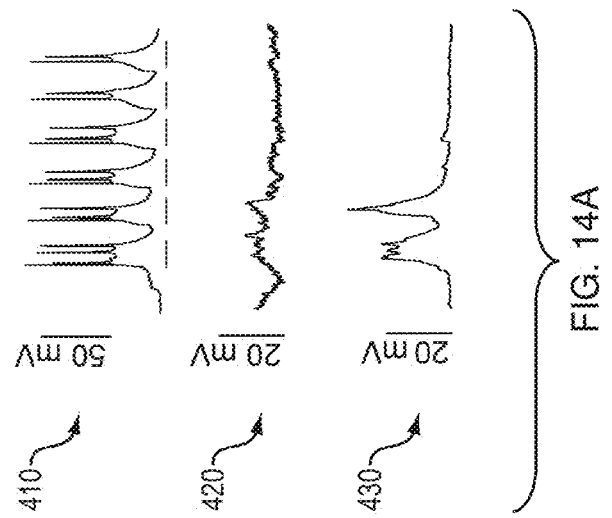

Currents were injected in the neurons recorded in FIGS. 13A-B to determine if they evoke synaptic currents in other neurons. FIGS. 14A-C are current traces showing the results of investigation of synaptic connectivity between whole cell patched neurons using the neurons recorded in FIGS. 13A-B. As shown in FIG. 14A, 80 pA of somatic current injection in the neuron shown in the top trace 410 elicited no response in the other two cells 420, 430 despite spiking. As shown in FIG. 14B, 120 pA current in the neuron recording shown in the middle trace 420, and in FIG. 14C, 60 pA current injection into the neuron recording shown in the bottom trace 430; again, no synaptic response was evoked in the other neurons. Evoked synaptic currents were not seen in any of the paired recordings, possibly because it was not within the range of distances where one would expect a high probability of synaptically connected neurons. This observation was consistent with other paired recordings.

Stable recording from multipatched cells for 56+8 minutes (n=23 neurons) was achieved, with recordings lasting for a maximum of 90 minutes. In the interest of throughput, the recordings were prematurely terminated in 5 trials (3 paired recordings, 2 single neuron recordings), before the whole cell recordings were lost, thus, the actual average recording time could have been higher.

Analyzing just the trials where multiple whole cell recordings were obtained, the mean and standard deviation of the access resistances obtained were 44.2+17.6 M$\Omega$ (n=23 neurons), the mean and standard deviation of the resting membrane potentials were −62.2+9.8 mV (n=23 neurons), and the mean and standard deviation of the currents needed to hold the neurons at −65 mV in voltage clamp mode was −78.5+55.2 pA (n=23 neurons). All of these values are comparable those obtained previously by us using the single channel autopatcher, suggesting that holding cells for prolonged periods of time (>2-3 minutes) did not affect the quality of the whole cell recordings.

The whole cell patched neurons were grouped into those that were gigasealed immediately upon detection, and those that were held in gigasealed states for longer periods of time during neuron hunting in other channels. Between these two groups, the access resistances and the resting membrane potentials were compared, being indicators of the quality of the recording obtained. All parameters reported here are in the uncompensated form (i.e. no series resistance or capacitance compensation), obtained using the conventional patch clamp software after autopatcher program completion. Previous literature has suggested that holding neurons for prolonged periods of time in gigaseal cell attached state leads to higher access resistances. Further, it was desired to assess the effect, if any, that tissue displacement had on these gigasealed neurons. The mean and standard deviation of the access resistances were 49.4+23.9 M$\Omega$ (n=8 cells that were successfully broken into immediately upon establishment of gigaseal), and 41.4+14.6 49.4+23.9 M$\Omega$ (n=15 cells that were gigasealed held in that state when other channels were conducting neuron hunting). No statistically significant difference was found in the access resistances of the two datasets (t-test, p>0.86).

Experimental Methods. Surgical procedures were conducted in a manner similar to those described previously in U.S. patent application Ser. No. 13/676,082. All animal procedures were approved by the MIT Committee on Animal Care. Adult male C57BL/6 mice (Taconic), 8-12 weeks old, were anesthetized using ketamine/xylazine (initially at 100 mg/kg and 10 mg/kg, and redosed at 30-45 minute intervals with 10-15% of the initial ketamine dose as needed, using toe pinch reflex as a standard metric of anesthesia depth). The scalp was shaved, and the mouse placed in a custom stereotax, with ophthalmic ointment applied to the eyes, and with Betadine and 70% ethanol used to sterilize the surgical area. Three self-tapping screws (F000CE094, Morris Precision Screws and Parts) were attached to the skull and a plastic headplate affixed using dental acrylic. Once set (~20 minutes), the mice were removed from the stereotax and placed in a custom-built low profile holder. A dental drill was used to open up 4 craniotomies (0.25-0.5 mm diameter, within a spacing of 1 mm) by thinning the skull until ~100 μm thick, and then a small aperture was opened up with a 30 gauge needle tip. Cortical craniotomies were opened at stereotaxic coordinates: anteroposterior, −1.5 to +0 mm relative to bregma; mediolateral, 1-3 mm left or right of the midline; neuron hunting typically began at a depth of ~400 μm depth. The dura was removed using a pair of fine forceps, or in some instances, not removed at all. For dampening the motion artifacts of the brain, 2% agarose was used to cover the brain surface. Experiments typically lasted 5 hours, at the end of which the mice were euthanized via cervical dislocation when fully anesthetized.

Electrophysiology. Borosilicate glass pipettes (Warner) with resistances between 3-9 MW were pulled using a filament micropipette puller (Flaming-Brown P97 model, Sutter Instruments) and stored in a closed petri dish to reduce dust contamination. During each experiment at least 60-70 pipettes were used. They were filled with intracellular pipette solution consisting of (in mM): 125 potassium gluconate (with more added empirically at the end, to bring osmolarity up to ~290 mOsm), 0.1 $CaCl_2$, 0.6 $MgCl_2$, 1 EGTA, 10 HEPES, 4 Mg ATP, 0.4 Na GTP, 8 NaCl (pH 7.23, osmolarity 289 mOsm), as used in the past.

Multipatcher robot operation. The first step of the process started with the pipettes having been installed in the holders. A program valve_reset.vi was executed in Labview to configure the pressure switching board to its default configuration, resulting in all pipettes being maintained in high positive pressure state. 3-axis linear actuators (Sutter Instruments) were employed to manually position the pipette tips over the craniotomy (or multiple craniotomies) 20-30 mm above the brain surface using a control joystick with the aid of a stereomicroscope (Nikon). The pipette voltage offsets were automatically nullified by the "pipette offset" function in the Multiclamp Commander (Molecular Devices) and the Multipatcher_ver1.0.vi program initiated.

The multipatcher represents the first demonstration of a scalable platform capable of conducting multidimensional single cell measurements at the neuronal circuit level. For the first time, a realistic solution for linking cellular level measurements to systems level characterization in the intact brain has emerged. The processes developed for the multipatcher build on the existing autopatcher process that has been previously reported (U.S. patent application Ser. No. 13/676,082, filed Nov. 13, 2012) and take into consideration the mechanical interactions of pipettes and the surrounding brain tissue while being actuated. The quality of recordings obtained with the mutlipatcher robot was comparable to the quality of recordings obtained with the single channel autopatcher system. When combined with custom hardware, it is thus scalable to control arbitrarily large numbers of pipettes in the intact brain. Further, if the hardware can be miniaturized with better precision in placement within much smaller regions spanning local microcircuits (<200 μm), it can be used to assess synaptic connectivity between neurons in a microcircuit in the intact brain. Multiple electrodes can also be used to record from varied interconnected regions of the brain, opening up possible experiments to assess how sub-threshold membrane potential fluctuations are correlated across these regions, such sensory thalamo-cortical circuits, or even more dynamic processes like memory formation.

The scalability in the electrode numbers means that the multipatcher can be used as a high-throughput tool for systematically obtaining large electrophysiological datasets for analyzing brain circuits. If combined with processes that enable automated single cell RNA harvesting, the robot can be used to probe and obtain genetic information from large numbers of cells. Such a strategy can be generalized to other frontiers in biology, bioengineering, and medicine, in which the assessment of the properties of single cells, embedded within intact tissue, is desired but has not previously been achievable in a systematic high-throughput fashion. For example, analyzing how different cells in a neural circuit respond to a drug in specific brain states, performing electrical characterizations of cells in tissues removed during surgery, determining how different individual cells within a tumor biopsy sample vary in gene expression, and assessing how tissue-engineered organs vary in cell to cell composition, may provide fundamental new capabilities in diagnostics, personalized medicine, and drug development.

Further, the hardware architecture makes it amenable to integration with optical components for optogenetic stimulation. This combined approach will enable assessments of the synaptic basis of how specific cell types coordinate network activity. The multipatcher opens up several interesting engineering challenges for scaling up. Currently, there are some limitations to the number of electrodes that can be simultaneously manipulated using these actuator systems due to their macroscopic scale. Attempting to build very large arrays using conventional apparatus would run into stereotactic hindrance within 6-12 pipettes. Alternate strategies for miniaturizing the actuation systems, as well as using novel electrodes such as flexible fused silica pipettes can be explored. Since patch pipettes can be used only once, scaled up multipatchers will require hundreds of pipettes to be fabricated, filled, and assembled for each experiment (60-70 pipettes are currently used in a typical day, taking ~1 hour to fabricate them). Thus developing a means to fabricate pipettes in an automated fashion can be advantageous. The time taken to assemble these pipette arrays will also increase proportionally with electrode numbers. Thus, strategies for automated filling and assembly of pipettes would be advantageous. Alternately, protocols can be developed to re-use assembled multipatcher arrays by attempting to clean pipettes tips or the hardware can be developed so as to allow robotic assembly of pipettes. Denser pipette arrays will increase the tissue displacement effects, and thus newer pipette geometries with thinner shanks, will be needed. Finally, as the number of channels increase, the cost of the amplifiers will be significant. Thus, use of low cost amplifiers dedicated for patch clamping would be advantageous in order to reduce the cost of patching.

While a preferred embodiment is disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention, which is not to be limited except by the claims that follow.

What is claimed is:

1. A method for automated multiple whole-cell patch clamping, comprising the steps of:
in an automated apparatus for multiple cell patch clamping that is under the control of a computer processor,
localizing a plurality of electrodes, each electrode of the plurality of electrodes having a tip and being associated with one of a plurality of cell patch clamping devices, by causing the tips of the electrodes to be moved to a predetermined location for cell hunting;
moving the tips of the plurality of electrodes by a defined amount;
making an electrical property measurement at each of the electrode tips during or after the step of moving;
determining whether or not a target cell has been encountered by one or more of the electrodes by constructing a temporal series of the electrical property measurements during or after at least one iteration of the steps of moving and making;
iteratively continuing the steps of moving, making, and determining until the temporal series of electrical property measurements for one or more of the electrodes, over a threshold number of consecutive iterations, indicates a predefined signature of electrode change that has passed a pre-set target cell detection threshold, wherein having a predefined signature of electrode change that passes the target cell detection threshold indicates that an electrode has encountered a target cell;
initiating connection formation for any electrodes that have encountered a target cell;
repeating the steps of continuing, pausing, and initiating until one or more of the plurality of electrodes has encountered a target cell; and
assessing whether or not connection formation has been achieved at the electrodes.

2. The method of claim 1, further comprising the step of:
if connection formation has been achieved, initiating break-in and formation of whole-cell patch clamps.

3. The method of claim 2, further comprising the step of verifying formation of the whole-cell patch clamps.

4. The method of claim 1, further comprising the steps of:
providing positive pressure to the cell patch clamping devices during the step of localizing; and
after completing the step of localizing,
reducing the pressure provided to the cell patch clamping devices to low positive pressure;
measuring the electrical property at the electrode tips;
assessing whether or not the electrical property has passed a pre-set tip blockage threshold at any of the electrode tips; and
if the electrical property has passed the pre-set tip blockage threshold for any of the electrode tips, retracting the associated cell patch clamping devices to indicate tip blockage and failure.

5. The method of claim 4, wherein the step of initiating connection formation further comprises the step of releasing the positive pressure applied to the cell patch clamping devices.

6. The method of claim 5, further comprising the steps of:
after the step of assessing, if connection formation has not been achieved for all tips, applying suction pressure to the cell patch clamping devices for which connection formation has not been achieved; and
re-assessing whether or not connection formation has been achieved for all tips.

7. The method of claim 2, wherein the step of initiating break-in and formation further comprises applying at least one of suction and an electrical pulse to the cell patch clamping devices.

8. The method of claim 1, further comprising the step of:
if a predetermined maximum level for moving the electrodes has been reached, retracting the cell patch clamping devices to indicate cell location failure.

9. A method for achieving and verifying multiple cell contact in an automated electrophysiology device, comprising the steps of:
in an automated electrophysiology apparatus that is under the control of a computer processor,
localizing a plurality of electrodes of the electrophysiology apparatus, each of the plurality of electrodes having a tip, by causing the tips of the electrodes to be moved to a predetermined location for cell hunting;

moving the tips of the plurality of electrodes by a defined amount;

making an electrical property measurement at each of the electrode tips during or after the step of moving;

determining whether or not a target cell has been encountered by any of the electrode tips by constructing a temporal series of the electrical property measurements during or after at least one iteration of the steps of moving and making; and iteratively continuing the steps of moving, making, and determining until the temporal series of electrical property measurements for one or more of the electrodes, over a threshold number of consecutive iterations, indicates a predefined signature of electrode change that has passed a pre-set cell detection threshold that indicates that cell contact has been achieved.

10. An apparatus for automated multiple cell patch clamping, comprising:

a cell patch formation apparatus, comprising:

a plurality of cell patch clamping devices, each cell patch clamping device comprising:

an associated electrode, the electrode having a tip and;

a 3-axis linear actuator configured for positioning the cell patch clamping device;

a patch amplifier with computer interface; and a programmable linear motor configured for moving the cell patch clamping devices up and down in a temporally precise fashion; and a computer interface configured for automated closed-loop control of the programmable linear motors based upon a temporal series of electrical property measurements made at the tips of the electrodes.

11. The apparatus of claim 10, further comprising an automated control system configured for:

causing the tips of the electrodes to be moved to a predetermined location for cell hunting;

iteratively causing the tips of the electrodes to be moved by a defined amount;

making an electrical property measurement at the electrode tips during or after each movement;

determining whether or not a target cell has been encountered by any of the electrode tips by constructing a temporal series of the electrical property measurements during or after at least one iteration of moving and making;

iteratively causing continuation of moving, making, and determining until the temporal series of electrical property measurements for one or more of the electrodes, over a threshold number of consecutive iterations, indicates a predefined signature of electrical change that has passed a pre-set cell detection threshold;

initiating connection formation; and assessing whether or not connection formation has been achieved at the electrodes.

12. The apparatus of claim 11, wherein the automated control system is further configured for initiating break-in and formation of whole-cell patch clamps if connection formation has been achieved and verifying formation of the whole-cell patch clamps.

13. The apparatus of claim 11, further comprising a controllable plurality of pneumatic valves configured for application of pressure and suction to the cell patch clamping devices.

14. The apparatus of claim 13, wherein the controllable plurality of pneumatic valves is configured for providing positive pressure to the cell patch clamping devices while the tips of the electrodes are moved to a predetermined location for cell hunting.

15. The apparatus of claim 13, wherein the controllable plurality of pneumatic valves is configured for reducing the pressure provided to the cell patch clamping device to low positive pressure after the tip of the electrode has been moved to a predetermined location for cell hunting; and the automated control system is further configured for:

measuring an electrical property at the electrode tips;

assessing whether or not the measured electrical property has passed a pre-set tip blockage threshold at any of the electrode tips; and if the measured electrical property has passed the pre-set tip blockage threshold for any of the electrode tips, directing the linear motor to retract the associated cell patch clamping device to indicate tip blockage and failure.

16. The apparatus of claim 15, wherein the controllable plurality of pneumatic valves is further configured for releasing the positive pressure applied to the cell patch clamping devices during initiation of connection formation.

17. The apparatus of claim 16, wherein the controllable plurality of pneumatic valves is further configured for applying suction pressure to the cell patch clamping devices if connection formation has not been achieved.

18. The apparatus of claim 16, wherein the controllable plurality of pneumatic valves further applies at least one of suction and an electrical pulse to the cell patch clamping devices to initiate break-in and whole-cell patch clamp formation.

19. A method for controlling an automated multiple cell patch clamping device, comprising the steps of:

in a cell patch formation apparatus, comprising:

a plurality of cell patch clamping devices, each having an associated electrode, the associated electrode having a tip;

a 3-axis linear actuator configured for positioning each cell patch clamping device;

a patch amplifier with computer interface;

a programmable linear motor configured for moving the cell patch clamping devices in a temporally precise fashion; and a computer interface configured for closed-loop control of the programmable motor based upon sequences of electrical property measurements made at the tips of the electrodes, localizing the electrodes by causing the linear motor to move the tip of the electrodes to a predetermined location for cell hunting;

causing the linear motor to iteratively move the tips of the electrodes by a defined amount;

measuring the electrical property at the electrode tips during or after the step of moving;

determining whether or not a target cell has been encountered by any of the cell patch clamping devices by constructing a temporal series of the electrical property measurements during or after at least one iteration of the steps of moving and measuring;

iteratively continuing the steps of moving, measuring, and determining until the temporal series of electrical property measurements for one or more of the electrodes, over a threshold number of consecutive iterations, indicates a predefined signature of electrode change that has passed a pre-set target cell detection threshold, wherein having a predefined signature of electrode change that passes the target cell detection threshold indicates that an electrode has encountered a target cell;

causing the linear motor to pause the electrodes;

initiating connection formation for any electrodes that have encountered a target cell;

assessing whether or not connection formation has been achieved;

if connection formation has been achieved, optionally initiating break-in and formation of at least one whole-cell patch clamp; and optionally verifying formation of the whole-cell patch clamps.

20. The method of claim 19, wherein the cell patch formation apparatus further comprises a controllable plurality of pneumatic valves configured for application of pressure and suction to the cell patch clamping devices and further comprising the steps of:

providing positive pressure from the controllable plurality of pneumatic valves to the cell patch clamping devices during the step of localizing;

after completing the step of localizing,
reducing the pressure provided to the cell patch clamping devices to low positive pressure;

measuring the electrical property at the electrode tips;

assessing whether or not the electrical property has passed a pre-set tip blockage threshold; and if the electrical property has passed the pre-set tip blockage threshold for any of the electrode tips, retracting the associated cell patch clamping device to indicate tip blockage and failure;

wherein the step of initiating connection formation further comprises releasing the positive pressure applied to the cell patch clamping devices;

after the step of assessing, if connection formation has not been achieved,
applying suction pressure from the controllable plurality of pneumatic valves to the cell patch clamping devices; and
re-assessing whether or not connection formation has been achieved; and wherein the step of initiating break-in and formation further comprises applying to the cell patch clamping devices at least one of: suction pressure from the controllable plurality of pneumatic valves and an electrical pulse.

* * * * *